US009575058B2

(12) United States Patent
Roy et al.

(10) Patent No.: US 9,575,058 B2
(45) Date of Patent: Feb. 21, 2017

(54) SYSTEMS AND METHODS OF FLUIDIC SAMPLE PROCESSING

(71) Applicant: Theranos, Inc., Palo Alto, CA (US)

(72) Inventors: Shaunak Roy, Palo Alto, CA (US); Malissa Takahashi, Palo Alto, CA (US); Ian Gibbons; Edmond Ku, Palo Alto, CA (US); Thanh Dang, Palo Alto, CA (US); Tammy Burd, Palo Alto, CA (US); Adam Vollmer, Palo Alto, CA (US); Elizabeth A. Holmes, Palo Alto, CA (US)

(73) Assignee: Theranos, Inc., Palo Alto, CA (US)

( * ) Notice: Subject to any disclaimer, the term of this patent is extended or adjusted under 35 U.S.C. 154(b) by 276 days.

(21) Appl. No.: 14/534,064

(22) Filed: Nov. 5, 2014

(65) Prior Publication Data

US 2015/0168384 A1     Jun. 18, 2015

Related U.S. Application Data

(63) Continuation of application No. 13/436,568, filed on Mar. 30, 2012, now Pat. No. 8,883,518, which is a continuation of application No. 12/221,816, filed on Aug. 6, 2008, now Pat. No. 8,158,430.

(60) Provisional application No. 60/954,301, filed on Aug. 6, 2007.

(51) Int. Cl.
| | |
|---|---|
| *C12M 1/34* | (2006.01) |
| *G01N 33/53* | (2006.01) |
| *G01N 33/49* | (2006.01) |
| *G01N 27/06* | (2006.01) |

(52) U.S. Cl.
CPC .......... *G01N 33/5302* (2013.01); *G01N 33/49* (2013.01); *G01N 27/06* (2013.01); *Y10S 435/973* (2013.01); *Y10S 436/809* (2013.01); *Y10T 436/106664* (2015.01)

(58) Field of Classification Search
None
See application file for complete search history.

(56) References Cited

U.S. PATENT DOCUMENTS

| | | | |
|---|---|---|---|
| 4,003,379 A | 1/1977 | Ellinwood, Jr. | |
| 4,146,029 A | 3/1979 | Ellinwood, Jr. | |
| 4,347,176 A | 8/1982 | Mehta | |
| 4,731,726 A | 3/1988 | Allen, III | |
| 4,793,825 A | 12/1988 | Benjamin et al. | |
| 4,910,131 A | 3/1990 | Mellman et al. | |
| 4,920,213 A | 4/1990 | Dale et al. | |

(Continued)

FOREIGN PATENT DOCUMENTS

| | | |
|---|---|---|
| CN | 2559986 | 7/2003 |
| JP | 2002511965 A | 4/2002 |

(Continued)

OTHER PUBLICATIONS

Bawendi, et al. The quantum-mechanics of larger semiconductor clusters. Annu. Rev. Phys. Chem. 1990; 41:477-496.

(Continued)

*Primary Examiner* — Chris L Chin

(57) ABSTRACT

The present invention provides fluidic devices and systems that allow detection of analytes from a biological fluid. The methods and devices are particularly useful for providing point-of-care testing for a variety of medical applications.

20 Claims, 23 Drawing Sheets

Assembly of Device

(56) References Cited

U.S. PATENT DOCUMENTS

| | | |
|---|---|---|
| 4,946,795 A | 8/1990 | Gibbons et al. |
| 5,104,813 A | 4/1992 | Besemer et al. |
| 5,162,237 A | 11/1992 | Messenger et al. |
| 5,279,607 A | 1/1994 | Schentag et al. |
| 5,472,603 A | 12/1995 | Schembri |
| 5,554,539 A | 9/1996 | Chadney et al. |
| 5,624,850 A | 4/1997 | Kumar et al. |
| 5,674,698 A | 10/1997 | Zarling et al. |
| 5,716,852 A | 2/1998 | Yager et al. |
| 5,744,366 A | 4/1998 | Kricka et al. |
| 5,797,898 A | 8/1998 | Santini et al. |
| 5,801,057 A | 9/1998 | Smart et al. |
| 5,807,375 A | 9/1998 | Gross et al. |
| 5,820,548 A | 10/1998 | Sieben et al. |
| 5,832,296 A | 11/1998 | Wang et al. |
| 5,842,787 A | 12/1998 | Kopf-Sill et al. |
| 5,848,991 A | 12/1998 | Gross et al. |
| 5,874,214 A | 2/1999 | Nova et al. |
| 5,885,470 A | 3/1999 | Parce et al. |
| 5,942,443 A | 8/1999 | Parce et al. |
| 5,961,451 A | 10/1999 | Reber et al. |
| 5,961,923 A | 10/1999 | Nova et al. |
| 5,976,896 A | 11/1999 | Kumar et al. |
| 5,980,830 A | 11/1999 | Savage et al. |
| 6,046,056 A | 4/2000 | Parce et al. |
| 6,074,616 A | 6/2000 | Buechler et al. |
| 6,123,861 A | 9/2000 | Santini, Jr. et al. |
| 6,156,181 A | 12/2000 | Parce et al. |
| 6,174,675 B1 | 1/2001 | Chow et al. |
| 6,176,962 B1 | 1/2001 | Soane et al. |
| 6,200,814 B1 | 3/2001 | Malmqvist et al. |
| 6,204,068 B1 | 3/2001 | Soini et al. |
| 6,221,677 B1 | 4/2001 | Wu et al. |
| 6,245,057 B1 | 6/2001 | Sieben et al. |
| 6,299,839 B1 | 10/2001 | Karunaratne et al. |
| 6,319,668 B1 | 11/2001 | Nova et al. |
| 6,340,588 B1 | 1/2002 | Nova et al. |
| 6,352,854 B1 | 3/2002 | Nova et al. |
| 6,368,275 B1 | 4/2002 | Sliwa et al. |
| 6,372,428 B1 | 4/2002 | Nova et al. |
| 6,375,469 B1 | 4/2002 | Brown |
| 6,429,025 B1 | 8/2002 | Parce et al. |
| 6,440,725 B1 | 8/2002 | Pourahmadi et al. |
| 6,464,687 B1 | 10/2002 | Ishikawa et al. |
| 6,482,593 B2 | 11/2002 | Walt et al. |
| 6,491,666 B1 | 12/2002 | Santini et al. |
| 6,503,231 B1 | 1/2003 | Prausnitz et al. |
| 6,527,762 B1 | 3/2003 | Santini, Jr. et al. |
| 6,542,717 B1 | 4/2003 | Zimmerman et al. |
| 6,544,732 B1 | 4/2003 | Chee et al. |
| 6,551,838 B2 | 4/2003 | Santini et al. |
| 6,591,124 B2 | 7/2003 | Sherman et al. |
| 6,632,216 B2 | 10/2003 | Houzego et al. |
| 6,649,358 B1 | 11/2003 | Parce et al. |
| 6,789,510 B1 | 9/2004 | Lee |
| 6,832,296 B2 | 12/2004 | Hooker |
| 6,849,237 B2 | 2/2005 | Housefield et al. |
| 6,878,755 B2 | 4/2005 | Singh et al. |
| 6,887,202 B2 | 5/2005 | Currie et al. |
| 6,923,764 B2 | 8/2005 | Aceti et al. |
| 6,927,851 B2 | 8/2005 | Mccaffrey et al. |
| 6,929,636 B1 | 8/2005 | Von Alten |
| 6,949,377 B2 | 9/2005 | Ho |
| 6,966,880 B2 | 11/2005 | Boecker et al. |
| 7,039,453 B2 | 5/2006 | Mullick et al. |
| 7,052,831 B2 | 5/2006 | Fletcher et al. |
| 7,105,183 B2 | 9/2006 | Mcgrath |
| 7,112,444 B2 | 9/2006 | Beebe et al. |
| 7,178,386 B1 | 2/2007 | Gamble et al. |
| 7,201,872 B2 | 4/2007 | Meron |
| 7,291,497 B2 | 11/2007 | Holmes et al. |
| 7,452,507 B2 * | 11/2008 | Renzi ............... B01L 3/502715 204/452 |
| 7,459,305 B2 | 12/2008 | Levy |
| 7,635,594 B2 | 12/2009 | Holmes et al. |
| 7,636,667 B2 | 12/2009 | Brown |
| 7,807,197 B2 | 10/2010 | Lee et al. |
| 7,888,125 B2 | 2/2011 | Gibbons et al. |
| 8,055,329 B2 | 11/2011 | Kimchy et al. |
| 8,158,430 B1 | 4/2012 | Roy et al. |
| 8,883,518 B2 | 11/2014 | Roy et al. |
| 2001/0019831 A1 | 9/2001 | Phillips et al. |
| 2001/0051340 A1 | 12/2001 | Singh et al. |
| 2001/0051766 A1 | 12/2001 | Gazdzinski |
| 2001/0053535 A1 | 12/2001 | Bashir et al. |
| 2002/0001854 A1 | 1/2002 | Lee |
| 2002/0034757 A1 | 3/2002 | Cubicciotti |
| 2002/0055094 A1 | 5/2002 | Reece et al. |
| 2002/0055127 A1 | 5/2002 | Gindilis |
| 2002/0072733 A1 | 6/2002 | Flaherty |
| 2002/0092770 A1 | 7/2002 | Hedberg et al. |
| 2002/0110496 A1 | 8/2002 | Samsoondar |
| 2002/0114739 A1 | 8/2002 | Weigl et al. |
| 2002/0132226 A1 | 9/2002 | Nair et al. |
| 2002/0143437 A1 | 10/2002 | Handique et al. |
| 2003/0014362 A1 | 1/2003 | Yim |
| 2003/0049833 A1 | 3/2003 | Chen et al. |
| 2003/0049865 A1 | 3/2003 | Santini et al. |
| 2003/0061687 A1 | 4/2003 | Hansen et al. |
| 2003/0069560 A1 | 4/2003 | Adamis et al. |
| 2003/0097092 A1 | 5/2003 | Flaherty |
| 2003/0104590 A1 | 6/2003 | Santini et al. |
| 2003/0117491 A1 | 6/2003 | Avni et al. |
| 2003/0143551 A1 | 7/2003 | Cattell |
| 2003/0148362 A1 | 8/2003 | Luka |
| 2003/0153900 A1 | 8/2003 | Aceti et al. |
| 2003/0167000 A1 | 9/2003 | Mullick et al. |
| 2003/0185706 A1 | 10/2003 | Ribi |
| 2003/0191430 A1 | 10/2003 | D'Andrea et al. |
| 2003/0208113 A1 | 11/2003 | Mault et al. |
| 2003/0208133 A1 | 11/2003 | Mault |
| 2003/0210607 A1 | 11/2003 | Gilbert et al. |
| 2003/0211007 A1 | 11/2003 | Maus et al. |
| 2003/0214057 A1 | 11/2003 | Huang |
| 2004/0005247 A1 | 1/2004 | Karp |
| 2004/0005582 A1 | 1/2004 | Shipwash |
| 2004/0033553 A1 | 2/2004 | Littarru et al. |
| 2004/0086872 A1 | 5/2004 | Childers et al. |
| 2004/0096959 A1 | 5/2004 | Stiene et al. |
| 2004/0121305 A1 | 6/2004 | Wiegand et al. |
| 2004/0122486 A1 | 6/2004 | Stahmann et al. |
| 2004/0213825 A1 | 10/2004 | Levy |
| 2004/0228766 A1 | 11/2004 | Witty et al. |
| 2004/0260204 A1 | 12/2004 | Boecker et al. |
| 2005/0009101 A1 | 1/2005 | Blackburn |
| 2005/0019836 A1 | 1/2005 | Vogel et al. |
| 2005/0054078 A1 | 3/2005 | Miller et al. |
| 2005/0064529 A1 | 3/2005 | Kwon |
| 2005/0090726 A1 | 4/2005 | Ackerman |
| 2005/0100937 A1 | 5/2005 | Holmes |
| 2005/0106713 A1 | 5/2005 | Phan et al. |
| 2005/0112544 A1 | 5/2005 | Xu et al. |
| 2005/0130292 A1 | 6/2005 | Ahn et al. |
| 2005/0130321 A1 | 6/2005 | Nicholson et al. |
| 2005/0136548 A1 | 6/2005 | Mcdevitt et al. |
| 2005/0137481 A1 | 6/2005 | Sheard et al. |
| 2005/0147559 A1 | 7/2005 | Von Alten |
| 2005/0209565 A1 | 9/2005 | Yuzhakov et al. |
| 2005/0221281 A1 | 10/2005 | Ho |
| 2005/0249633 A1 | 11/2005 | Blatt et al. |
| 2005/0255001 A1 | 11/2005 | Padmanabhan et al. |
| 2005/0255600 A1 | 11/2005 | Padmanabhan et al. |
| 2006/0019319 A1 | 1/2006 | Billadeau et al. |
| 2006/0029924 A1 | 2/2006 | Brewster et al. |
| 2006/0062852 A1 | 3/2006 | Holmes |
| 2006/0078998 A1 | 4/2006 | Puskas et al. |
| 2006/0106316 A1 | 5/2006 | Palti |
| 2006/0177873 A1 | 8/2006 | Dowd et al. |
| 2006/0182738 A1 | 8/2006 | Holmes |
| 2006/0211933 A1 | 9/2006 | Zimmermann et al. |
| 2006/0257941 A1 | 11/2006 | Mcdevitt et al. |
| 2006/0264779 A1 | 11/2006 | Kemp et al. |
| 2006/0264780 A1 | 11/2006 | Holmes et al. |
| 2006/0264782 A1 | 11/2006 | Holmes et al. |

(56) References Cited

U.S. PATENT DOCUMENTS

| | | | |
|---|---|---|---|
| 2006/0264783 | A1 | 11/2006 | Holmes et al. |
| 2007/0166195 | A1 | 7/2007 | Padmanabhan et al. |
| 2007/0224084 | A1 | 9/2007 | Holmes et al. |
| 2007/0264629 | A1 | 11/2007 | Holmes et al. |
| 2008/0009766 | A1 | 1/2008 | Holmes et al. |
| 2008/0113391 | A1 | 5/2008 | Gibbons et al. |
| 2010/0074799 | A1 | 3/2010 | Kemp et al. |
| 2010/0081144 | A1 | 4/2010 | Holmes et al. |
| 2010/0248277 | A1 | 9/2010 | Gibbons et al. |
| 2011/0003699 | A1 | 1/2011 | Yoder et al. |
| 2011/0104826 | A1 | 5/2011 | Gibbons et al. |
| 2011/0166553 | A1 | 7/2011 | Holmes et al. |
| 2012/0034598 | A1 | 2/2012 | Holmes et al. |
| 2013/0115685 | A1 | 5/2013 | Holmes et al. |

FOREIGN PATENT DOCUMENTS

| | | | |
|---|---|---|---|
| JP | 2002538440 | A | 11/2002 |
| JP | 2004527825 | A | 9/2004 |
| WO | 9401165 | A | 1/1994 |
| WO | 0135928 | A | 5/2001 |
| WO | 0164344 | A2 | 9/2001 |
| WO | 03066128 | A | 8/2003 |
| WO | 2005024437 | A1 | 3/2005 |
| WO | 2005031355 | A | 4/2005 |
| WO | 2005065157 | A | 7/2005 |
| WO | 2005121367 | A | 12/2005 |
| WO | 2007120904 | A | 10/2007 |

OTHER PUBLICATIONS

BD Biosciences, Directigen FluA&B Assay Manual. Oct. 11, 2016, pp. 1-11.
Beier, et al. Versatile derivatisation of solid support media for covalent bonding on DNA-microchips. Nucleic Acids Res. 1999; 27:1970-1977.
Bes, et al. Mapping the paratope of anti-CD4 recombinant Fab 13B8.2 by combining parallel peptide synthesis and site-directed mutagenesis. J Biol Chem. Apr. 18, 2003;278(16):14265-73.
Bhatia, et al. Use of thiol-terminal silanes and heterobifuntional crosslinkers for immobilization of antibodies on silica surfaces. Anal Biochem. 1989; 178(2):408-13.
Broadcaster Moira Gunn with Elizabeth Holmes, recorded Mar. 5, 2005 on Biotech Nation.
Bruchez, et al. Semiconductor nanocrystals as fluorescent biological labels. Science. 1998; 281(5385):2013-6.
Celebre, et al. A comparative sudy of efficiencies of fibre optic and prism TIRF sensors. Meas. Sci. Technol. 1992; 3:1166-1173.
Chan. Quantum dot bioconjugates for ultrasensitive nonisotopic detection. Science. 1998;281(5385):2016-8.
Chang, et al. Micromachining & Microfabrication. SPIE Optical Engineering Press. Bellingham, Wash. 1997. (Cover pages and table of contents only).
Charles, et al. Synthesis of a flurescent analog of polychlorinated biphenyls for use in a continuous flow immunosensor assay. Bioconjug Chem. 1995; 6(6):691-4.
Duffy, et al. Rapid Prototyping of Microfluidic Systems in Poly(dimethylsiloxane). Analytical Chemistry. 1998; 70 (23);4974-4084.
European search report and search opinion dated Feb. 7, 2012 for EP Application No. 11180769.9.
European search report and search opinion dated Mar. 6, 2012 for EP Application No. 10179887.4.
European search report and search opinion dated May 29, 2012 for EP Application No. 11180769.9.
European search report dated Jun. 2, 2009 for Application No. 07762092.
Gavin, et al. Review of Rapid Diagnostic Tests for Influenza. Clinical and Applied Immunology Reviews. 2004; 4 (3):151-172.
Geddes, et al. The impedance of stainless-steel electrodes. Med Biol Eng. Sep. 1971;9(5):511-21.
Harlow, et al. Antibodies: A Laboratory Manual. Cold Spring Harbor Laboratory. New York. 1988. (Cover pages and table of contents only).
Harrison's Principles of Internal Medicine, Part 2 Cardinal Manifestations of Disease, Ch. 60 (12th ed. 1991; pp. 338-343.).
Hirsh, et al. The electrical conductivity of blood. I: Relationship to erythrocyte concentration. Blood. Nov. 1950;5 (11):1017-35.
International search report dated Jan. 22, 2008 for PCT/US06/42563.
International search report dated Dec. 8, 2008 for PCT/US06/11090.
International search report dated Jul. 4, 2005 for PCT/US04/029462.
International search report dated Aug. 11, 2008 for PCT/US07/68665.
International search report dated Sep. 9, 2008 for PCT/US07/23904.
Jaeger. Introduction to Microelectronic fabrication. Addison-Wesley Publishing Co. Reading Mass. 1988. (Cover pages and table of Contents only).
Kessler, et al. Use of the DNA flow-thru chip, a three-dimensional biochip, for typing and subtyping of influenza viruses. J Clin Microbiol. May 2004;42(5):2173-85.
Kilbourne, et al. Independent and disparate evolution in nature of influenza A virus hemagglutinin and neuraminidase glycoproteins. Proc Natl Acad Sci U S A. Jan. 1990;87(2):786-90.
Lee, et al. Microfluidic enzyme-linked immunosorbent assay technology. Adv Clin Chem. 2006;42:255-95.
Liu, et al. Validation of a fully integrated microfluidic array device for influenza A subtype identification and sequencing. Anal Chem. Jun. 15, 2006;78(12):4184-93.
Lupiani, et al. Improved diagnostic tests for Avian influenza surveillance, 2005. Proceedings of the Institute of Food Technologies' First Annual Forod protection and Defense Research Conference.
Mohapatra, et al. Blood resistivity and its implications for the calculation of cardic output by the thoracic electrical impedance technique. Intensive Care Med. Aug. 1977;3(2):63-7.
Mukerjee, et al. Microneedle array for transdermal biological fluid extraction and in situ analysis. Sensors and Actuators A. 2004; 114:267-275.
Notice of Allowability dated Sep. 12, 2014 for U.S. Appl. No. 13/436,568.
Office Action dated Jan. 5, 2010 for U.S. Appl. No. 11/388,415.
Office Action dated Jan. 8, 2013 for U.S. Appl. No. 11/388,415.
Office Action dated Oct. 17, 2008 for U.S. Appl. No. 11/389,410.
Office Action dated Oct. 26, 2006 for U.S. Appl. No. 10/937,872.
Office Action dated Oct. 6, 2008 for U.S. Appl. No. 11/746,535.
Office Action dated Nov. 22, 2011 for U.S. Appl. No. 11/202,231.
Office Action dated Nov. 5, 2009 for U.S. Appl. No. 11/202,231.
Office Action dated Nov. 9, 2011 for U.S. Appl. No. 11/388,823.
Office Action dated Dec. 11, 2012 for U.S. Appl. No. 12/750,518.
Office Action dated Dec. 19, 2008 for U.S. Appl. No. 11/202,206.
Office Action dated Dec. 22, 2009 for U.S. Appl. No. 11/388,823.
Office Action dated Dec. 22, 2010 for U.S. Appl. No. 11/554,509.
Office Action dated Feb. 1, 2013 for U.S. Appl. No. 13/187,960.
Office Action dated Feb. 17, 2009 for U.S. Appl. No. 11/202,231.
Office Action dated Feb. 2, 2011 for U.S. Appl. No. 11/746,535.
Office Action dated Feb. 22, 2008 for U.S. Appl. No. 11/202,231.
Office Action dated Feb. 22, 2008 for U.S. Appl. No. 11/746,535.
Office Action dated Feb. 27, 2009 for U.S. Appl. No. 11/388,723.
Office Action dated Mar. 16, 2011 for U.S. Appl. No. 11/202,231.
Office Action dated Mar. 17, 2009 for U.S. Appl. No. 11/388,415.
Office Action dated Mar. 18, 2008 for U.S. Appl. No. 11/202,206.
Office Action dated Mar. 21, 2008 for U.S. Appl. No. 11/388,723.
Office Action dated Mar. 21, 2011 for U.S. Appl. No. 11/388,415.
Office Action dated Mar. 22, 2010 for U.S. Appl. No. 11/202,206.
Office Action dated Mar. 3, 2011 for U.S. Appl. No. 11/202,206.
Office Action dated Mar. 5, 2009 for U.S. Appl. No. 11/388,823.
Office Action dated Mar. 5, 2010 for U.S. Appl. No. 11/746,535.
Office Action dated Mar. 7, 2006 for U.S. Appl. No. 10/937,872.
Office Action dated Apr. 1, 2010 for U.S. Appl. No. 11/388,824.
Office Action dated Apr. 13, 2012 for U.S. Appl. No. 11/554,509.
Office Action dated Apr. 18, 2007 for U.S. Appl. No. 10/937,872.

(56) References Cited

OTHER PUBLICATIONS

Office Action dated Apr. 29, 2009 for U.S. Appl. No. 11/389,409.
Office Action dated Apr. 30, 2009 for U.S. Appl. No. 11/388,824.
Office Action dated Apr. 30, 2013 for U.S. Appl. No. 13/647,325.
Office Action dated Apr. 4, 2013 for U.S. Appl. No. 12/986,954.
Office Action dated Apr. 5, 2010 for U.S. Appl. No. 11/554,509.
Office Action dated Apr. 8, 2009 for U.S. Appl. No. 11/389,410.
Office Action dated May 22, 2009 for U.S. Appl. No. 11/746,535.
Office Action dated Apr. 29, 2012 for U.S. Appl. No. 12/986,954.
Office Action dated Jun. 1, 2007 for U.S. Appl. No. 11/389,409.
Office Action dated Jun. 1, 2012 for U.S. Appl. No. 11/388,823.
Office Action dated Jun. 11, 2012 for U.S. Appl. No. 11/388,415.
Office Action dated Jun. 21, 2007 for U.S. Appl. No. 11/202,231.
Office Action dated Jun. 9, 2010 for U.S. Appl. No. 11/746,535.
Office Action dated Jul. 18, 2012 for U.S. Appl. No. 12/576,197.
Office Action dated Jul. 25, 2008 for U.S. Appl. No. 11/389,409.
Office Action dated Jul. 27, 2011 for U.S. Appl. No. 11/554,509.
Office Action dated Jul. 28, 2009 for U.S. Appl. No. 11/202,206.
Office Action dated Jul. 29, 2011 for U.S. Appl. No. 12/986,954.
Office Action dated Aug. 24, 2010 for U.S. Appl. No. 11/388,415.
Office Action dated Aug. 27, 2010 for U.S. Appl. No. 11/388,823.
Office Action dated Aug. 29, 2008 for U.S. Appl. No. 11/388,823.
Office Action dated Aug. 31, 2011 for U.S. Appl. No. 12/221,816.
Office Action dated Sep. 1, 2005 for U.S. Appl. No. 10/937,872.
Office Action dated Sep. 11, 2008 for U.S. Appl. No. 11/389,409.
Office Action dated Sep. 22, 2011 for U.S. Appl. No. 12/576,197.
Office Action dated Sep. 5, 2008 for U.S. Appl. No. 11/388,723.
Pal, et al. An integrated microfluidic device for influenza and other genetic analyses. Lab Chip. Oct. 2005;5 (10):1024-32. Epub Aug. 18, 2005.
Patolsky, et al. Electrical detection of single viruses. Proc Natl Acad Sci USA. Sep. 28, 2004;101(39):14017-22. Epub Sep, 13, 2004.
Pescovitz, D. Sniffing out airborne disease. Lab Note: Research from the College of Engineering, University of California, Berkeley, 2004. Available online at http://www.coe.berkeley.edu/labnotes/0904/pisano.html. Accessed Jan. 28, 2011.
Preininger, et al. Polymer-coated optical fibres for application in a direct evanescent wave immunoassay. Analytica Chimica Acta, 2000; 403; 67-76.
Rai-Choudhury, ed., Handbook of Microlithography, Micromachining & Microfabrication. SPIE Optical Engineering Press. Bellingham, Wash. 1997. (Cover pages and table of contents only).
Red Herring. Stopping bad reactions. Red Herring. Dec. 26, 2005.
Runyan, et al. Seminconductor integrated circuit processing technology. Addison-Wesley Publishing Co., Reading Mass. 1990. (Cover pages and table of contents only).
Sambrook, et al. Molecular Cloning: A Laboratory Manual. Cold Spring Harbor Laboratory Press. New York. 2001. (Cover pages and table of contents only).
Sapsford, et al. Demonstration of four immunoassay formats using the array biosensor. Anal Chem. 2002; 74 (5):1061-8.
Scheurle, et al. HER-2/neu expression in archival non-small cell lung carcinomas using FDA-approved hercep test. Anticancer Res. 2000; 20:2091-2096.
Spira, et al. The identification of monoclonal class switch variants by sib selection and an ELISA assay. J Immunol Methods. 1984;74(2):307-15.
Steplewski, et al. Isolation and characterization of anti-monosialoganglioside monoclonal antibody 19-9 class-switch variants. Proc Natl Acad Sci U S A. 1985; 82(24):8653-7.
Stevens, et al. Glycan microarray analysis of the hemagglutinins from modern and pandemic influenza viruses reveals different receptor specificities. J Mol Biol. Feb. 3, 2006;355(5):1143-55.
Tedeschi, et al. Antibody immobilisation on fibre optic TIRF sensors. Biosens Bioelectron. 2003; 19(2):85-93.
U.S. Appl. No. 13/286,168, filed Oct. 31, 2011. Inventors: Holmes et al.
U.S. Appl. No. 13/366,193, filed Feb. 3, 2012. Inventors: Holmes et al.
U.S. Appl. No. 13/629,577, filed Sep. 27, 2012. Inventors: Holmes et al.
Yan, et al. Multiplexed flow cytometric immunoassay for influenza virus detection and differentiation. Anal Chem. Dec. 1, 2005;77(23):7673-8.

* cited by examiner

Assembly of Device

Sample Dilution Syringe

Bottom Part of Device

Vial Assembly 10x blood = No rbc separation 10x lysed blood = No rbc separation, all cells lysed

SYSTEMS AND METHODS OF FLUIDIC SAMPLE PROCESSING

CROSS REFERENCE

This application is a continuation application of U.S. application Ser. No. 12/221,816 filed on Aug. 6, 2008 which claims priority to U.S. Provisional Application No. 60/954,301 filed on Aug. 6, 2007, all of which are incorporated herein by reference in their entirety.

BACKGROUND OF THE INVENTION

The discovery of a vast number of disease biomarkers and the establishment of miniaturized microfluidic systems have opened up new avenues to devise methods and systems for the prediction, diagnosis and treatment of diseases in a point-of-care setting. Point-of-care testing is particularly desirable because it rapidly delivers results to medical practitioners and enables faster consultation. Early diagnosis allows a practitioner to begin treatment sooner and thus avoiding unattended deterioration of a patient's condition.

In many diagnostic devices that perform immunoassays, dilution of the test sample prior to running the assay is preferable for a variety of reasons. For example, sample dilution can help removal of matrix effects, unbind the target molecules from other binding proteins in the sample, bring the target analyte concentration into the measurable range of the assay, and/or provide sufficient liquid to perform multiple assays (especially when the available sample is small, such as a drop of fluid). In most cases, the dilution must be exquisitely precise or risk compromising the precision of the assay result. Devices such as those constructed by Abaxis (U.S. Pat. No. 5,472,603), Biotrack (U.S. Pat. Nos. 4,946,795 and 5,104,813), and Miles (U.S. Pat. No. 5,162,237) typically perform dilutions precise to about 2%; however, such devices may require a large volume of test sample, which is more difficult to obtain in a point-of-care setting.

Often, when measuring a blood sample, analytes in serum or plasma are of interest. One reason is that many analytes are found in the fluid part of blood namely plasma. For numerous blood tests performed for clinical purposes, the final reported concentration typically needs to relate to the concentration of blood serum or blood plasma in a diluted sample. In most cases, blood serum or blood plasma is the test medium of choice in the lab. Two operations may be necessary prior to running an assay, dilution and red blood cell removal. Blood samples vary significantly in the proportion of the sample volume occupied by red cells (the hematocrit which varies from about 20-60%). Furthermore, in a point-of-care environment when assay systems are operated by non-expert personnel, the volume of sample obtained may not be that which is intended. If a change in volume is not recognized, it can lead to error in the reported analyte concentrations.

Thus, there remains a considerable need for point-of-care devices that can provide accurate and rapid data collection, transmission, analysis, and/or real-time medical consultation or decision making. In particular, there remains a need in the art for a point-of-care fluidic device that can measure the concentration of plasma in a sample, and determined the apparent dilution ratio to effect an accurate quantification of an analyte of interest present in a small sample of blood. The present invention satisfies these needs and provides related advantages as well.

SUMMARY OF THE INVENTION

In an aspect of the invention, a fluidic device for detecting the presence or absence of an analyte in a bodily fluid from a subject comprises a sample collection unit, an assay assembly, and a calibration unit, wherein the sample collection unit contains a diluent and is removable from the device. In an embodiment, the sample collection unit is configured to collect a sample of bodily fluid from a subject. In an embodiment, the assay assembly comprises at least one reaction site containing a reactant that reacts with an analyte to yield a detectable signal indicative of the presence of the analyte.

In another embodiment, a device comprises a calibration unit, wherein the calibration unit is configured to provide a measurement of a sample used for calibrating a detectable signal.

In a further aspect of the invention, a fluidic device is disclosed for detecting the presence or absence of an analyte in a bodily fluid from a subject comprising a sample collection unit, an assay assembly, and a calibration unit. The sample collection unit is configured to collect said sample of bodily fluid from said subject. The assay assembly comprises at least one reaction site containing a reactant that reacts with the analyte to yield a detectable signal indicative of the presence of the analyte. The calibration unit is configured to provide a measurement of said sample used for calibrating said detectable signal.

In an embodiment, the measurement of a sample is used for determining concentration of the detected analyte.

In another embodiment, a sample collection unit of the device allows a sample of bodily fluid to react with a reactant contained within an assay assembly based on a protocol transmitted from an external device.

In some embodiments, a sample of bodily fluid is a blood sample. Preferably, the sample is less than 50 microliters. In an embodiment, the sample is a single drop of fluid.

In an embodiment, the sample collection unit is removable from the device. In another embodiment, the sample collection unit is further configured to dilute a sample. The sample collection unit can contain a diluent for diluting a sample.

In another embodiment, the sample collection unit is further configured to remove a part of a sample. For example, the unit can remove cells from a sample such as blood.

In an embodiment, a reaction site within an assay assembly is immobilized in a fluidic channel. In an embodiment of the device, the reaction site receives reagents from a first direction and a sample of bodily fluid from a second direction. The reagents and the sample can be delivered to the reaction site by syringe action.

In an embodiment, the device conducts an immunoassay. The reagents for carrying out the reaction comprise immunoassay reagents. In an embodiment, the detectable signal yielded at a reaction site is a luminescent signal. The device can also be configured to detect a plurality of analytes useful for assessing efficacy and/or toxicity of a therapeutic agent.

In another embodiment, a calibration unit of the device is configured to measure the conductivity of a sample. To measure the conductivity of a sample, the device can comprise electrodes. In a preferable embodiment, the electrodes are positioned within a fluidic channel.

In an embodiment, the sample collection unit, assay assembly, and calibration unit can also be configured for one time use.

In an embodiment, the device of the invention further comprises a waste chamber.

In another aspect of the invention, a system for detecting an analyte in a bodily fluid from a subject is disclosed. The system comprises a fluidic device of the invention, a reader assembly comprising a detection assembly for detecting a signal, and a communication assembly for transmitting the signal to an external device.

In an embodiment, a sample collection unit of the system of the invention allows a sample of bodily fluid to react with reactants contained within an assay assembly based on a protocol transmitted from an external device to yield a detectable signal indicative of the presence of an analyte. In a further embodiment, the protocol is transmitted wirelessly from an external device. In another embodiment, a fluidic device further comprises an identifier to provide the identity of said fluidic device that is adapted to trigger the transmission of a protocol.

In an embodiment, a system of the invention is configured to detect a plurality of analytes useful for assessing efficacy and/or toxicity of a therapeutic agent.

In an aspect of the invention, a method of detecting an analyte in a bodily fluid from a subject is disclosed, which comprises providing a fluidic device or system of the invention, allowing a portion of a sample to react with assay reagents contained within an assay assembly of the device to yield a signal indicative of the presence of an analyte in the sample, and detecting the signal generated from the analyte collected in the sample of bodily fluid.

In an embodiment, a method of the invention comprises calibrating the measurement of a signal generated from an analyte in a sample based upon a measurement by a calibration unit of an embodiment of a device of the invention. In a further embodiment, an additional step of quantifying the amount of an analyte present in a bodily fluid based on the measurement provided by the calibration unit can be executed.

In an embodiment, a fluidic device can detect a plurality of analytes and the fluidic device comprises immunoassay reagents for the plurality of analytes.

In an aspect of the invention a method of measuring plasma concentration of a blood sample comprises providing a plasma sample substantially free of removing red blood cells, passing a current through the plasma sample, and measuring at least one of conductivity or impedance of the plasma sample, thereby measuring the plasma concentration of said blood sample.

In an embodiment, the blood sample is diluted with a diluent prior to passing a current through the plasma sample.

In an embodiment, measuring of plasma concentration occurs in a fluidic channel.

In another embodiment, a method of measuring plasma concentration of a blood sample comprises comparing the measured conductivity to a set of predetermined values showing relationship of conductivity values and plasma concentrations.

In an embodiment, a method of measuring plasma concentration of a blood sample comprises comparing the measured conductivity to a set of predetermined values showing relationship of conductivity values and dilution ratios that are employed to dilute the blood sample. In a further embodiment, the set of predetermined values is a calibration curve. The calibration curve can be normalized. In some embodiments, normalizing accounts for at least one factor selected from the group consisting of surface area of an electrode, temperature of the sample, gain of a circuit wherein the circuit delivers the current to the sample, volume of the sample, and red blood cell quantity of the sample.

In an aspect, a method of calculating an apparent dilution ratio utilized in diluting a blood sample for running a blood test comprises providing a plasma sample derived from a diluted blood sample, measuring conductivity of the plasma sample, and comparing the measured conductivity to a set of predetermined values showing relationship of conductivity values and dilution ratios that are employed to dilute a blood sample, thereby calculating the apparent dilution ratio.

In an embodiment of the method of the invention, the blood sample is diluted prior to running the blood test.

In another embodiment, the plasma sample derived from a diluted blood sample is substantially free of red blood cells.

In an embodiment, the conductivity of the plasma sample is inversely proportional to the apparent dilution ratio.

The present invention also provides a business method of monitoring a clinical trial of a therapeutic agent, comprising: a) collecting at least one pharmacological parameter from a subject in said clinical trial at a plurality of time intervals, said collecting step is effected at each time interval by subjecting a sample of bodily fluid from said subject to reactants contained in the fluidic device of claim 1, wherein said fluidic device is provided to said subject to yield detectable signals indicative of the values of said at least one pharmacological parameter at a plurality of time intervals; b) comparing the detected values to a threshold value predetermined for said pharmacological parameter; c) notifying a clinician and/or a sponsor involved in said clinical trial when a statistically significant discrepancy exists between the detected values and the threshold value. In one embodiment, the business method involves the step of taking a medical action based on the statistically significant discrepancy. Such method action can involve adjusting dosage of the therapeutic agent, continuing, modifying, or terminating the clinical trial.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Fluidic Devices and Systems

Figure 1:
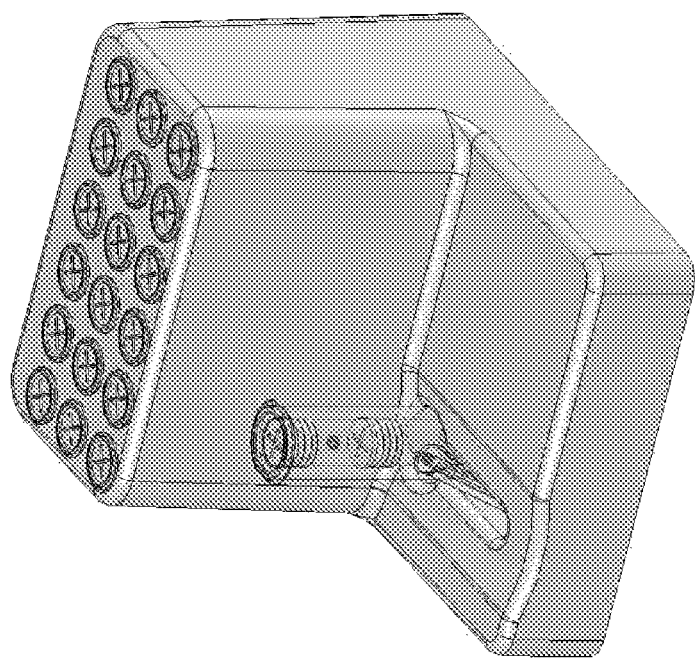
FIG. 1 illustrates a device for fluidic sample processing.

One aspect of the present invention is a system for detecting an analyte in a sample of bodily fluid. The system is capable of detecting and/or quantifying analytes that are associated with specific biological processes, physiological conditions, disorders or stages of disorders, or effects of biological or therapeutic agents.

In an aspect, a fluidic device for detecting the presence or absence of an analyte in a bodily fluid from a subject comprises a sample collection unit and an assay assembly, wherein the sample collection unit contains a diluent and is removable from the device. In an embodiment, the sample collection unit is configured to collect a sample of bodily fluid from a subject. In an embodiment, the assay assembly comprises at least one reaction site containing a reactant that reacts with an analyte to yield a detectable signal indicative of the presence of the analyte.

In another embodiment, a device comprises a calibration unit, wherein the calibration unit is configured to provide a measurement of a sample used for calibrating a detectable signal.

The system comprises a fluidic device having one or more of the following components: a sample collection unit, an assay assembly, and a calibration unit. The sample collection unit is configured to collect a sample of bodily fluid from a subject. The assay assembly comprises at least one reaction site containing a reactant that reacts with an analyte from the bodily fluid, which yields a detectable signal indicative of the presence of the analyte.

In general, the calibration unit is configured to provide a measurement of the sample used for calibrating the detected signal. For example, the calibration unit can be any unit or device part that measures a parameter for calibrating the measurement of the concentration of an analyte in a sample. Exemplary calibration units can provide without limitation volume measurement, flow measurement, and cell count. In one aspect, measurement provided by the calibration unit is used for determining the concentration of the detected analyte. For example, where a diluted blood sample is used for detecting analyte present in the plasma portion, the calibration unit provides a measurement of the diluted plasma concentration, and hence the apparent dilution ratio which is then in turn used for determining the initial concentration of the analyte of interest.

Any bodily fluids suspected to contain an analyte of interest can be used in conjunction with the system or devices of the invention. Commonly employed bodily fluids include but are not limited to blood, serum, saliva, urine, gastric and digestive fluid, tears, stool, semen, vaginal fluid, interstitial fluids derived from tumorous tissue, and cerebrospinal fluid.

A bodily fluid may be drawn from a patient and brought into the fluidic device in a variety of ways, including but not limited to, lancing, injection, or pipetting. In one embodiment, a lancet punctures the skin and draws the sample into the fluidic device using, for example, gravity, capillary action, aspiration, or vacuum force. The lancet may be part of the fluidic device, or part of a reader assembly, or as a stand alone component. Where needed, the lancet may be activated by a variety of mechanical, electrical, electromechanical, or any other known activation mechanism or any combination of such methods. In another embodiment where no active mechanism is required, a patient can simply provide a bodily fluid to the fluidic device, as for example, could occur with a saliva sample. The collected fluid can be placed in the sample collection unit within the fluidic device. In yet another embodiment, the fluidic device comprises at least one microneedle which punctures the skin. The microneedle can be used with a fluidic device alone, or can puncture the skin after the fluidic device is inserted into a reader assembly.

The volume of bodily fluid to be used with a fluidic device of the present invention is generally less than about 500 microliters, typically between about 1 to 100 microliters. Where desired, a sample of 1 to 50 microliters, 1 to 40 microliters, 1 to 30 microliters, 1 to 10 microliters or even 1 to 3 microliters can be used for detecting an analyte using the subject fluidic device.

In an embodiment, the volume of bodily fluid used for detecting an analyte utilizing the subject devices or methods is one drop of fluid. For example, one drop of blood from a pricked finger can provide the sample of bodily fluid to be analyzed with a fluidic device system or method of the invention.

In some embodiments, the bodily fluids are used directly for detecting the analytes present therein with the subject fluidic device without further processing. Where desired, however, the bodily fluids can be pre-treated before performing the analysis with the subject fluidic devices. The choice of pre-treatments will depend on the type of bodily fluid used and/or the nature of the analyte under investigation. For instance, where the analyte is present at low level in a sample of bodily fluid, the sample can be concentrated via any conventional means to enrich the analyte. Methods of concentrating an analyte include but are not limited to drying, evaporation, centrifugation, sedimentation, precipitation, and amplification. Where the analyte is a nucleic acid, it can be extracted using various lytic enzymes or chemical solutions according to the procedures set forth in Sambrook et al. ("Molecular Cloning: A Laboratory Manual"), or using nucleic acid binding resins following the accompanying instructions provided by manufacturers. Where the analyte is a molecule present on or within a cell, extraction can be performed using lysing agents including but not limited to denaturing detergent such as SDS or non-denaturing detergent such as Thesit, sodium deoxylate, triton X-100, and tween-20.

In an embodiment, pretreatment can include diluting and/or mixing the sample. In addition, the pretreatment can include filtering the sample to remove, for example, red blood cells from a blood sample. In one aspect, the subject systems and fluidic devices are provided with the capability of on-board sample pretreatment, including without limitation dilution, concentration, and separation of a particular sample fraction (for example, separating bodily fluid from cells contained therein).

In an embodiment, the sample is diluted in a ratio that is satisfactory for a both a high sensitivity and low sensitivity assays. For example, a dilution ratio of sample to diluent can be in the range of about 1:100-1:1. In another example, the dilution ratio is about 1:15.

In an embodiment, the device of the invention is self-contained and contains all reagents (liquid and solid-phase) required to perform several quantitative immunoassays in a short period of time. The device can use a small volume of bodily fluid, for example, a single drop. In an embodiment, the bodily fluid is blood and can be obtained by a fingerstick. The device can be operated by a small instrument. Different functions of that can be carried out by the device include, but are not limited to, dilution of a sample, removal of parts of a sample (for example, red blood cells (RBCs), fluidic routing of a sample to an assay assembly, routing of the liquid reagents to the assay assembly, and containing liquids during and following use of the device. The device can also include an optical interface.

In some embodiments, the sample collection unit is configured to collect a sample of bodily fluid from the subject and to deliver a predetermined portion of the sample to be assayed by the assay assembly. In this manner, the device automatically meters the appropriate volume of the sample that is to be assayed. In an embodiment, the sample collection unit can comprise a sample collection well and/or a sample dilution syringe. Generally, the sample dilution syringe collects bodily fluid from the patient.

FIG. 1 illustrates an exemplary system of the present invention. In the embodiment illustrated in FIG. 1, a sample dilution syringe (SDS) is inserted into a fully assembled device. The fluidic device of the invention may take a variety of configurations, including a single-use unit. In an exemplary system, the device contains the reactants necessary to perform one or more assays in a plurality of vials within the device. The vials can contain one or more reactants, a wash buffer, or a combination thereof. In other examples, reagents with a relatively short shelf-life can be supplied separately and be utilized, for example, by the end user.

A sample collection unit in a fluidic device may provide a bodily fluid sample from a patient by any of the methods described above. Where desired, the sample may first be processed by diluting the bodily fluid, and or may be filtered by separating the plasma from the red blood cells. In some embodiments there may be more than one sample collection unit in the fluidic device.

Figure 2:
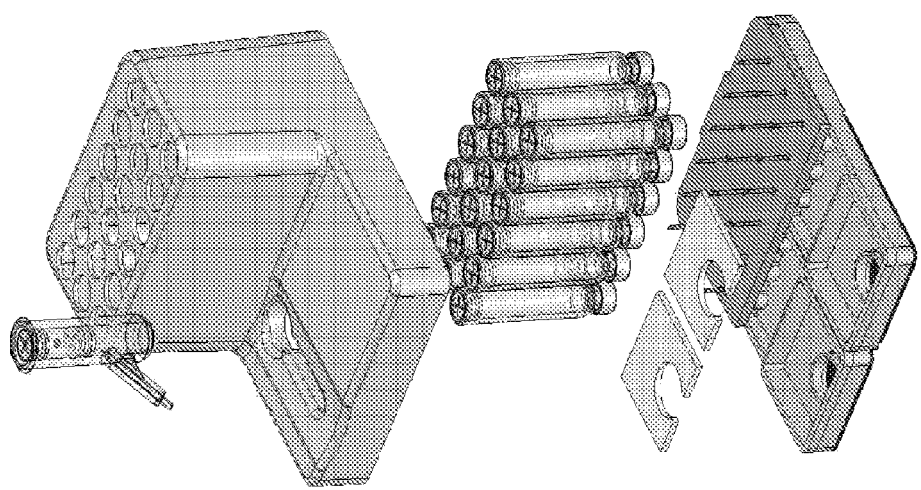
FIG. 2 illustrates the components of a device for fluidic sample processing and demonstrates some relationships between the components.
Figure 3:
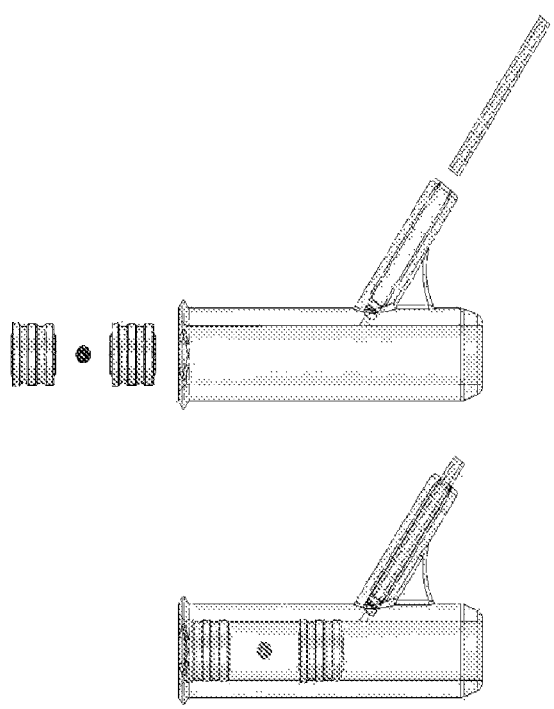
FIG. 3 illustrates a sample collection unit containing a diluent.
Figure 4:
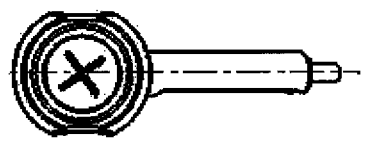
FIG. 4 illustrates a sample dilution syringe for collecting and diluting a sample with a diluent.
Figure 4:
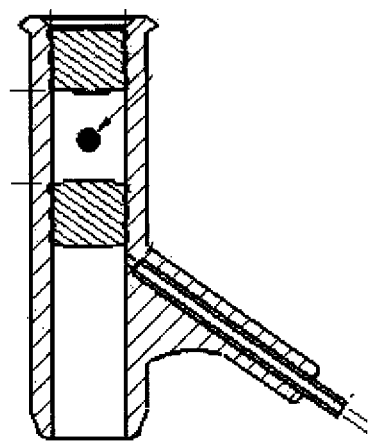

FIG. 2 illustrates exemplary layers of a fluidic device according to the present invention prior to assembly of the fluidic device. The sample collection unit can be a sample dilution syringe for sample acquisition and capable of diluting a sample that is inserted into the body of the device. The sample dilution syringe can contain a capillary tube, which press-fits into the housing of the sample dilution syringe. The capillary tube can be made from a variety of materials, including plastic or a variety of polymeric materials such as polystyrene, polycarbonate, polypropylene, polydimethysiloxanes (PDMS), polyurethane, polyvinylchloride (PVC), and polysulfone, or glass, or semi-conducting material such as silicon and its derivatives. The tube can also be optionally coated with anti-coagulant. An example of the sample dilution syringe is illustrated in FIGS. 3 and 4.

In some embodiments the inner surface of the capillary tube, the sample dilution syringe, and/or the sample collection unit may be coated with a surfactant and/or an anti-coagulant solution. The surfactant provides a wettable surface to the hydrophobic layers of the fluidic device and facilitate filling of the capillary tube and sample dilution syringe with a liquid sample, for example, blood. The anti-coagulant solution helps prevent a sample, for example, blood, from clotting when provided to the fluidic device. Exemplary surfactants that can be used include without limitation, Tween, Triton, Pluronics and other non-hemolytic detergents that provide the proper wetting characteristics of a surfactant. EDTA and heparin are non-limiting anti-coagulants that can be used.

In one embodiment, a coating can be made a solution comprising, for example, 2% Tween, 25 mg/mL EDTA in 50% Methanol/50% $H_2O$, which is then air dried. A methanol/water mixture provides a means of dissolving the EDTA and Tween, and also dries quickly from the surface of the material. The solution can be applied to the layers of the fluidic device by any means that will ensure an even film over the surfaces to be coated, such as pipetting, spraying, printing, or wicking.

The housing of the sample dilution syringe comprises a tube. In the tube, two movable seals can contain a volume of a diluent. In an embodiment, the volume of the diluent is predetermined, for example, in about the range of 50 microliters to 1 ml, preferably in the range of about 100 microliters to 500 microliters.

The diluent is preferably a buffered solution containing anti-coagulant, sugar, antibodies to a common red cell antigen. The diluent can also contain a dispersion of magnetizable particles to which are bound antibodies typically directed to red cell antigen. The housing can also contain a mixing ball that can aid in re-suspending the magnetizable particles.

In some embodiments the housing includes a movable mixing element that causes the mixing of the predetermined portion of the sample with the diluent. Exemplary movable mixing element is with a general ball shape. The movable mixing elements may have any shape, such as, for example, a cube shape.

In one embodiment the movable mixing element is magnetically controlled, for example, a magnetically controlled ball in the mixing chamber that, when magnetically controlled, will cause the mixing of the predetermined portion of the sample and the diluent. The ball can be about 5% of the combined volume of the sample and diluent. The ball can be magnetically controlled to move in a reciprocal, linear fashion, within the mixing chamber. The ball may be pre-magnetized or unmagnetized, but susceptible to magnetic forces.

The movable mixing element can be contained in the sample dilution syringe or in a sample collection well. It is also contemplated that the mixing element might operate outside of the fluidic device, such as if the reader assembly were adapted to agitate the fluidic device and thereby mix the predetermined portion of sample and the diluent.

In some embodiments the sample collection unit further comprises a filter configured to filter the diluted sample before it is assayed.

Figure 5:
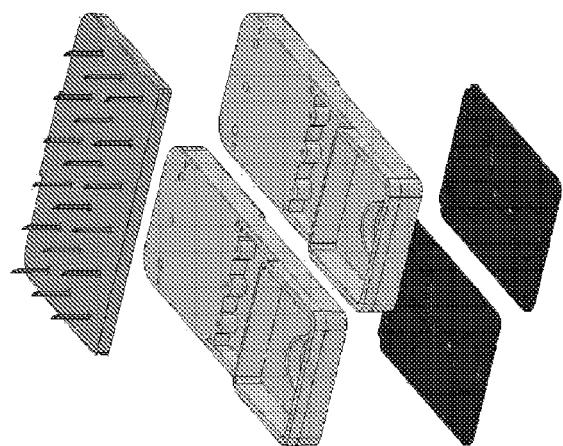
FIG. 5 illustrates a part of a device for fluidic sample processing comprising a cartridge, a liquid routing manifold, and a sample collection well.

FIG. 2 also illustrates a bottom part covered by the body of an exemplary device and below the sample collection unit. An exemplary bottom part of the device is illustrated in FIG. 5 which contains a clear material bottom, an assay assembly unit, a liquid reagent distribution manifold, and reagent containers. The clear bottom part can comprise energy directors, which enable ultrasonic welding to the assay assembly unit. When the two parts are welded together, they can define a fluid path. In a preferable embodiment, the fluid path comprises a calibration unit, followed by at least one assay assembly. In an embodiment, a plurality of assay assemblies (two, three, four, five, six, or more) is incorporated into the device. Multiple assay assemblies preferably constitute optically and chemically isolated zones.

Also illustrated in FIG. 5 is a cartridge body with features that form a fluid channel connecting a sample collection well that is designed to hold a diluted sample to an assay assembly. Where desired, the cartridge can be made of substantially opaque material. In a preferable embodiment, the opaque cartridge body is constructed of a white material, for example, white plastic. The features of the cartridge can include a Greek letter Psi-shaped channel and "vias" (through holes) that are in fluid communication with reagent reservoirs.

At least one of the fluidic channels will typically have small cross sectional dimensions. In some embodiments the dimensions are from about 0.01 mm to about 5 mm, preferably from about 0.03 mm to about 3 mm, and more preferably from about 0.05 mm to about 2 mm. Fluidic channels in the fluidic device may be created by, for example without limitation, precision injection molding, laser etching, embossing or any other technique known in the art to carry out the intent of the invention.

Figure 6:
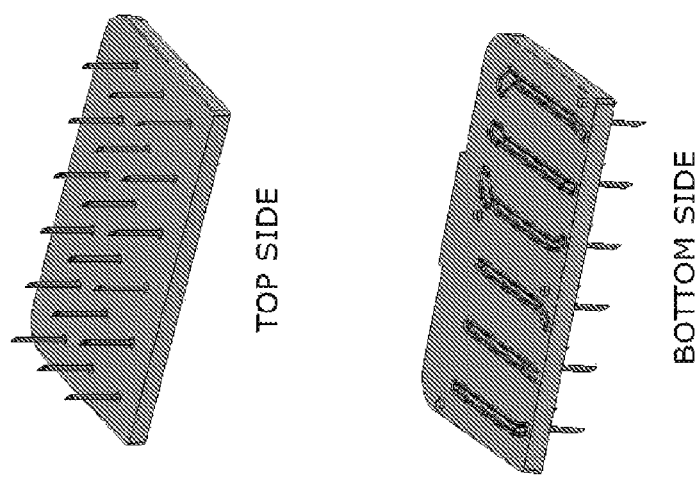
FIG. 6 illustrates a liquid routing manifold for routing reagents to a cartridge for sample processing.

Reagent reservoirs contained within a device of the invention can be coupled to the assay assembly for delivering the reagents to the assembly. One method of coupling the reagent reservoirs and the assay assembly is by utilizing a distribution manifold. FIG. 6 demonstrates an embodiment of a liquid reagent distribution manifold fitted with a set of needles that engage with reagent reservoirs. The manifold comprises needles or pins for coupling to a vial containing a reagent.

Figure 7:
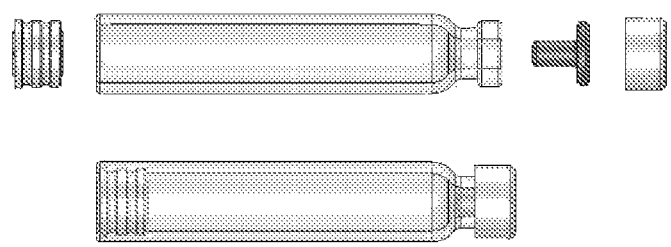
FIG. 7 illustrates a vial for containing reagents for fluidic sample processing and demonstrates the assembly of the vial.

FIG. 2 illustrates a set of vertically oriented cylindrical reagent reservoirs or vials. In an embodiment, the reagent reservoirs are constructed of glass. The vials can be fitted with one upper movable seal and a lower septum. The lower septum can be held in place by a crimpable metal cap. Liquid reagents can be contained the seal and the lower septum. In one version of the invention, during manufacture of the device, the lower septum of each reagent reservoir is pierced the corresponding needles without the needles penetrating into the liquid compartments. An example of a vial useful for constructing the device of the invention is illustrated in FIG. 7.

In a preferred embodiment there is at least one reagent reservoir. In some embodiments there is any number of reagent reservoirs as are necessary to fulfill the purposes of the invention. A reagent reservoir is preferably in fluid communication with at least one reaction site, and the reagents contained in the reagent reservoirs can be released into the fluidic channels within the fluidic device.

In an embodiment, the reagent reservoir contains a plurality of reagents. The plurality of reagents can be separated from each other, to avoid interaction between the reagents. In a further embodiment, a reagent reservoir contains a plurality of movable seals. For example, there may be four movable seals. Three voids can be created between the movable seals and the voids can be filled with a reagent. The seals can be moved by pump or syringe-like action. If there is a hole, for example, in the side of the reagent reservoir, each void can be moved into position with the hole, and a reagent contained within the void is then released through the hole to the reaction site. As such, the reagent reservoir can contain all of the agents or wash buffers necessary for a single assay.

Reagents according to the present invention include without limitation wash buffers, enzyme substrates, dilution buffers, conjugates, enzyme-labeled conjugates, DNA amplifiers, sample diluents, wash solutions, sample pretreatment reagents including additives such as detergents, polymers, chelating agents, albumin-binding reagents, enzyme inhibitors, enzymes, anticoagulants, red-cell agglutinating agents, antibodies, or other materials necessary to run an assay on a fluidic device. An enzyme conjugate can be either a polyclonal antibody or monoclonal antibody labeled with an enzyme that can yield a detectable signal upon reaction with an appropriate substrate. Non-limiting examples of such enzymes are alkaline phosphatase and horseradish peroxidase. In some embodiments the reagents comprise immunoassay reagents. In general, reagents especially those that are relatively unstable when mixed with liquid are confined in a defined region (for example, a reagent reservoir) within the subject fluidic device. The containment of reagents can be effected by valves that are normally closed and designed for one-time opening, preferably in a unidirectional manner.

In some embodiments a reagent reservoir contains approximately about 10 μl to about 1 ml of fluid. In some embodiments the chamber may contain about 100-500 μl of fluid. The volume of liquid in a reagent chamber may vary depending on the type of assay being run or the sample of bodily fluid provided. In an embodiment, the volumes of the reagents do not have to predetermined, but must be more than a known minimum. In some embodiments the reagents are initially stored dry and dissolved upon initiation of the assay being run on the fluidic device.

In an embodiment, the reagent reservoir can be filled using a syringe, a needle, or a combination thereof. The reagent reservoirs may be filled with fluid using a fill channel and a vacuum draw channel.

In an embodiment of the invention, multiple vials are utilized to isolate reagents from each other. The vials may also be used to contain a wash solution. In addition, the vials may be used to contain a luminogenic substrate.

Another embodiment can feature a reagent reservoir vial, a wash solution vial, and a luminogenic substrate vial all in relation to the same assay assembly.

Figure 8:
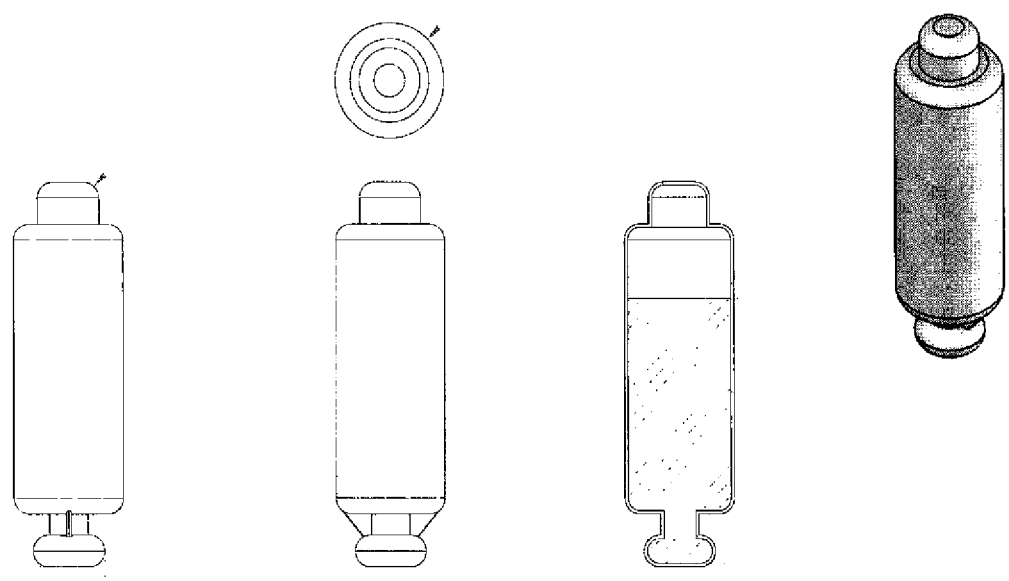
FIG. 8 illustrates a reagent container formed by blow molding.

Other configurations of reservoirs are contemplated such as collapse-able (concertina-like) plastic vials made of, for example, polypropylene or polyethylene. An example of the collapse-able plastic vials is illustrated in FIG. 8.

Figure 9:
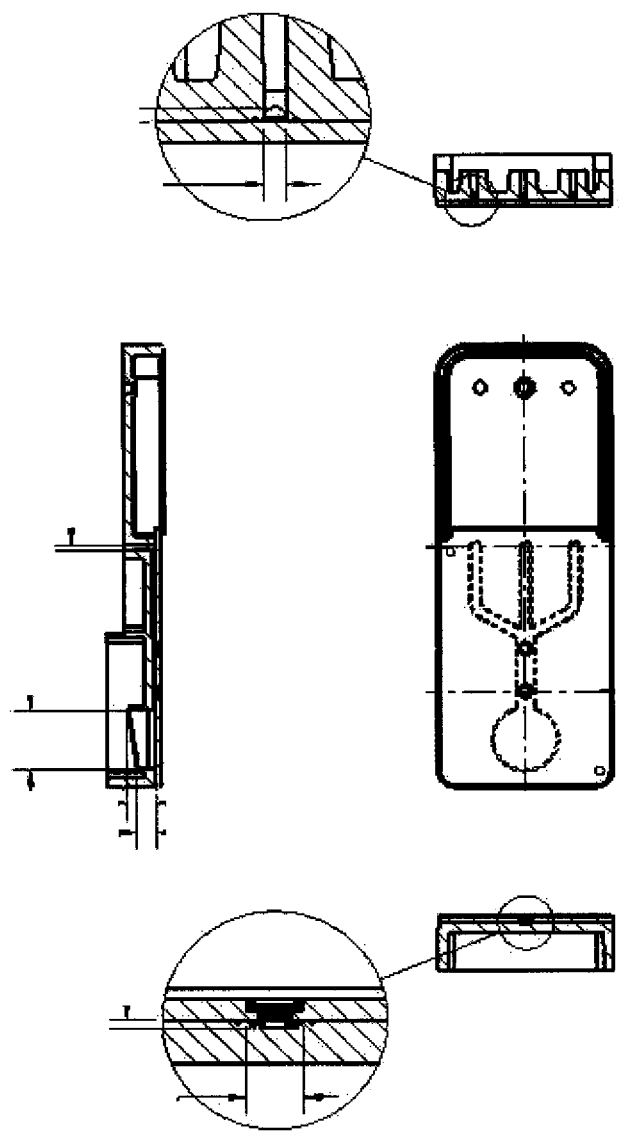
FIG. 9 demonstrates a cartridge for sample processing.

The cartridge of the device as shown in FIG. 2 comprises an assay assembly. The assay assembly comprises a "capture surface" or reaction site, may be placed on any of several locations within the cartridge. Another view of the cartridge is illustrated in FIG. 9. The assay assembly can be located in the "vias" of the cartridge. In an embodiment, the assay assembly is located on the clear cartridge bottom. In a preferable embodiment, the assay assembly is located on or in a fluidic channel feature of the cartridge body.

The reaction site can be bound covalently or by adsorption antibodies to an area of the device. The surface is then dried and maintained in dry condition until used in an assay. In an embodiment, there is one reaction site for each analyte to be measured.

In preferred embodiments the reagent reservoirs and sample collection unit are fluidly connected to reaction sites where bound probes can detect an analyte of interest in the bodily fluid sample using the assay. A reaction site could then provide a signal indicative of the presence of the analyte of interest, which can then be detected by a detection device described in detail herein below.

In an alternative embodiment, the capture surface can be located in a fluidic channel. In an embodiment, the reaction site can be located in three, horizontally oriented, fluidic channels. The reaction site can be immobilized to either the clear bottom surface and/or the cartridge body. In another embodiment, the reaction site can be located in the vias of a device of the invention. The vias are fluidly connected to the fluidic channel and to the reagent manifold.

In an embodiment, a reaction site can be on a channel that was made separately and inserted into or onto the device. One version of this approach utilizes molded polystyrene surfaces with the inner surface coated with a reaction site, wherein the surfaces can be fitted into or adjacent to the channels or vias of the device. Similarly, a reaction site can be coated onto the inside of cylindrical polystyrene tubes which are press fitted into a fluid channel or fitted into a via. These molded surfaces can provide an assay capture surface that can be made and evaluated before the assembly of the cartridge for bulk manufacturing for one-time use and replacement of the reaction site. In another embodiment, a molded plastic piece can be placed in the device of the present disclosure by a variety of methods. For example, it can be compressed into a fluid channel. In another example, the reaction site can be fit into a cavity in a fluidic channel with inlets and outlets smaller than the reaction site (for example, a cavity is formed when two parts of the disposable are welded together). Some advantages of this embodiment include, but are not limited to, eliminating press fit methods; and making large quantities of the reaction site as mentioned previously. The reaction site may be quality controlled before assembly of the overall cartridge.

In another alternative embodiment, an object can be placed into a via or fluid channel of the device. The object within a via or fluid channel can be coated with a capture surface, creating a reaction site of the invention. The object can be placed in the vias or channels of the device before, during, or after device construction and incorporating the reaction site into the device. In one embodiment, molded plastic (such as polystyrene) pieces such as spheres, beads, elliptical forms, torroidal elements, and the like are either commercially available or can be made by injection molding with precise shapes and sizes. For example, the characteristic dimension can be in the 0.05-3 mm range. These pieces can be coated with capture reagents using a method similar to those used to coat microtiter plates but with the advantage that they can be processed in bulk by placing them in a large vessel, adding coating reagents and processing using sieves and the like to recover the pieces and wash them as needed. In this way, a large number of reaction sites can be manufactured on the vias or the channels of the microfluidic device for mass production of the devices.

In another embodiment, an area of the device comprises projections that are coated with capture reagents to carry out an assay with the device of the invention.

In some embodiments the reactions sites are flat but they may take on a variety of alternative surface configurations. The reaction site preferably forms a rigid support on which a reactant can be immobilized. The reaction site surface is also chosen to provide appropriate characteristics with respect to interactions with light. For instance, the reaction site may be functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, polypropylene, or combinations thereof. Other appropriate materials may be used in accordance with the present invention. A transparent reaction site may be advantageous. In addition, in the case where there is an optically transmissive 'window" permitting light to reach an optical detector, the surface may be advantageously opaque and preferentially light scattering.

A reactant immobilized at a reaction site can be anything useful for detecting an analyte of interest in a sample of bodily fluid. For instance, such reactants include without limitation nucleic acid probes, antibodies, cell membrane receptors, monoclonal antibodies and antisera reactive with a specific analyte. Various commercially available reactants such as a host of polyclonal and monoclonal antibodies specifically developed for specific analytes can be used.

One skilled in the art will appreciate that there are many ways of immobilizing various reactants onto a support where reaction can take place. The immobilization may be covalent or non-covalent, via a linker moiety, or tethering them to an immobilized moiety. These methods are well known in the field of solid phase synthesis and micro-arrays (Beier et al., Nucleic Acids Res. 27:1970-1-977 (1999). Non-limiting exemplary binding moieties for attaching either nucleic acids or proteinaceous molecules such as antibodies to a solid support include streptavidin or avidin/biotin linkages, carbamate linkages, ester linkages, amide, thiolester, (N)-functionalized thiourea, functionalized maleimide, amino, disulfide, amide, hydrazone linkages, and among others. In addition, a silyl moiety can be attached to a nucleic acid directly to a substrate such as glass using methods known in the art. Surface immobilization can also be achieved via a Poly-L Lysine tether, which provides a charge-charge coupling to the surface.

In some embodiments there are more than one reaction sites which can allow for detection of multiple analytes of interest from the same sample of bodily fluid. In some embodiments there are 2, 3, 4, 5, 6, or more reaction sites, or any other number of reaction sites as may be necessary to carry out the intent of the invention.

In embodiments with multiple reaction sites on a fluidic device, each reaction site may be immobilized with a reactant different from a reactant on a different reaction site. In a fluidic device with, for example, three reaction sites, there may be three different probes, each bound to a different reaction site to bind to three different analytes of interest in the sample. In some embodiments there may be different reactants bound to a single reaction site if, for example, a CCD with multiple detection areas were used as the detection device, such that multiple different analytes could be detected in a single reaction site. The capability to use multiple reaction sites in addition to multiple different probes on each reaction site enables multiple analyte measurement characteristics of the present invention.

The present invention allows for the detection of multiple analytes on the same fluidic device. If assays with different luminescent intensities are run in adjacent reaction sites, photons (signals that emanate from the reactions) may travel from one reaction site to an adjacent reaction site, as reaction sites may be constructed of materials that allow photons to travel through the fluidic channels that connect the sites. This optical cross talk may compromise the accuracy of the detected photons. Different embodiments of this invention can eliminate or reduce the amount of optical cross-talk. Non-linear channels prevent photons to pass through. Additionally, the edges or walls of a reaction site may be constructed using optically opaque or light scattering materials so that light will not escape. In some embodiments the reaction sites are white or opaque.

In some embodiments, unbound signal-generating conjugates may need to be washed from a reaction site to prevent unbound conjugates from activating the substrate and producing and inaccurate signal. It may be difficult to remove conjugates sticking to the edges of the reaction sites in such a fluidic device if, for example, there is not an excess of a wash solution. To decrease the signal contributed from unbound conjugates stuck to the edge of a reaction site, it may be advantageous to expand the reaction site edge or wall radius in order to distance non-specifically bound conjugate from the desired actual detection area, represented by bound reactant.

When using a wash buffer in an assay, the device can store buffer in vials in fluid communication with the reaction site. In an embodiment, the wash reagent is able to remove reagent from the reaction sites by about 99.9% by washing. In general, a high washing efficiency resulting in a high degree of reduction of undesired background signals is preferred. Washing efficiency is typically defined by the ratio of signal from a given assay to the total amount of signal generated by an assay with no wash step and can be readily determined by routine experimentation. It is generally preferred to increase the volume of washing solution and time of incubation but without sacrificing the signals from a given assay. In some embodiments, washing is performed with about 200 ul to about 5000 ul of washing buffer, preferably between about 250 ul to about 1000 ul washing buffer, for about 10 to about 300 seconds. To facilitate this efficiency, the sides of the reaction sites are adapted for smooth flow of the reagents and for minimal boundary layer effects. Where desired, the channels connecting the reaction sites can be configured as a chicane so as to reduce cross-talk of any kind and also uncontrolled fluid flow.

Additionally, it can be advantageous to use several cycles of small volumes of wash solution which are separated by periods of time where no wash solution is used. This sequence allows for diffusive washing, where labeled antibodies diffuse over time into the bulk wash solution from protected parts of the assay such as the well edges or surfaces where it is loosely bound and can then be removed when the wash solution is moved from the reaction site.

Where desired, the subject systems and fluidic devices can be configured to contain any reagents necessary to perform an assay on a fluidic device according to the present invention on-board, or housed within the fluidic device before, during, and after the assay. In this way the only inlet or outlet from the fluidic device is preferably the bodily fluid sample initially provided by the fluidic device. This design also helps create an easily disposable fluidic device where all fluids or liquids remain in the device. The on-board design also prevents leakage from the fluidic device into the reader assembly which should remain free from contamination from the fluidic device.

In embodiments of the invention the fluidic device includes at least one waste chamber to trap or capture all liquids after they have been used in the assay. In an embodiment, there is more than one waste chamber, at least one of which is to be used with a calibration assembly described herein below. On-board waste chambers also allow the device to be easily disposable. The waste chamber is preferably in fluidic communication with at least one reaction site.

In addition, a bubble trapper can be positioned between a sample collection unit and reaction site. The bubble trapper can have such geometry that the bubbles tend to migrate towards the edges of this surface and remain stuck at that service, thereby not entering into the reaction sites.

The size of the channels in the fluidic device can reduce the amount of air that enters the reaction sites. As the reagent passes through, the width of a first channel is about double the width of a channel leading to the reaction sites. The potential for air to enter into the channel leading to the reaction sites is reduced or eliminated as the air would be forced to squeeze in the smaller channel.

In some embodiments the fluidic device comprises valves that prevent backflow through the circuitry. During assays the volume, velocity, and timing of the liquid movement can be controlled. Assays may incorporate prolonged incubations where very little, if any, liquid movement should occur. During these stages no or substantially no back-flow of liquid should occur in the fluidic device.

In certain applications of the subject systems or fluidic devices, calibration of the detected signal is desirable in order to ascertain the concentration of an analyte present in the initial sample of bodily fluid under investigation. Accordingly, in a featured embodiment of the present invention, the calibration unit can be any unit or device part that measures a quantity for calibrating the measurement of the concentration of an analyte in a sample. Example calibration units include, but are not limited to, a volume measurement, a flow measurement, and a cell counter. In a preferable embodiment of the invention there is a separate control circuit which provides known quantities of analytes that can be measured in parallel with analytes in the sample. In another embodiment, the sample is mixed with a known quantity of a substance not found in a sample, and a measurement of the added substance is made. By comparison of the known added analyte quantity with that measured, the analyte "recovery" can be determined and used to correct possible errors in measurements of analytes in the sample.

To measure the quantity of plasma in a diluted sample, it is often desirable to measure the apparent dilution ratio (sample plasma to final volume of diluted plasma). In an embodiment, the conductivity of the diluted sample can be measured to determine the apparent dilution ratio. For measurement of conductivity of a test sample, at least two electrodes are typically placed adjacent to a fluidic channel between the sample collection well and the assay assembly. The electrodes may or may not be in fluid communication with the fluidic channel. In an embodiment, the electrodes are adjacent to the same surface of the fluidic channel. The cartridge illustrated in FIG. 9 demonstrates two electrodes in a fluidic channel between a sample collection well and the reaction sites. The electrodes can be spaced at different distances in the fluidic channel. The spacing and size of the electrodes has an effect on the measurement of electrical conductivity of a sample as discussed later herein. Where desired, the electrodes can be connected to a control circuit when the methods and systems of the invention are executed.

Depending on the intended application, it may be advantageous to measure conductivity in a control as a means to check the measurement system. For example, the control part is exposed to reagents of known conductivity provided by the manufacturer.

In some embodiments, a sensor for assessing the reliability of an assay for an analyte in a bodily fluid with the use of the subject fluidic device can be provided together with the fluidic device, the reader and/or within the packaging of the subject system. The sensor is capable of detecting a change in operation parameters under which the subject system normally operates. The operation parameters include but are not limited to temperature, humidity, and pressure, which may affect the performance of the present system.

A fluidic device and reader assembly may, after manufacturing, be shipped to the end user, together or individually. As a reader assembly is repeatedly used with multiple fluidic devices, it may be necessary to have sensors on both the fluidic device and reader assembly to detect such changes during shipping, for example. During shipping, pressure or temperature changes can impact the performance of a number of components of the present system, and as such a sensor located on either the fluidic device or reader assembly can relay these changes to, for example, the external device so that adjustments can be made during calibration or during data processing on the external device. For example, if the temperature of a fluidic device is changed to a certain level during shipping, a sensor located on the fluidic device could detect this change and convey this information to the reader assembly when it is inserted into the reader assembly by the user. There may be an additional detection device in the reader assembly to perform this, or such a device may be incorporated into another system component. In some embodiments this information may be wirelessly transmitted to either the reader assembly or the external device. Likewise, a sensor in the reader assembly can detect similar changes. In some embodiments, it may be desirable to have a sensor in the shipping packaging as well, either instead of in the system components or in addition thereto.

Manufacturing of the fluidic channels may generally be carried out by any number of microfabrication techniques that are well known in the art. For example, lithographic techniques are optionally employed in fabricating, for example, glass, quartz or silicon substrates, using methods well known in the semiconductor manufacturing industries such as photolithographic etching, plasma etching or wet chemical etching. Alternatively, micromachining methods such as laser drilling, micromilling and the like are optionally employed. Similarly, for polymeric substrates, well known manufacturing techniques may also be used. These techniques include injection molding or stamp molding methods where large numbers of substrates are optionally produced using, for example, rolling stamps to produce large sheets of microscale substrates or polymer microcasting techniques where the substrate is polymerized within a micromachined mold.

In some embodiments at least one of the different layers of the fluidic device may be constructed of polymeric substrates. Non limiting examples of polymeric materials include polystyrene, polycarbonate, polypropylene, polydimethysiloxanes (PDMS), polyurethane, polyvinylchloride (PVC), and polysulfone.

The subject fluidic devices can comprise a waste chamber that contains unreacted reagents. Where desired, the waste chamber can contain an absorbent material comprises at least one quenching agent which reacts with at least one reagent from said assay assembly to reduce interference of the optical signal indicative of the presence of the analyte in the sample. The quenching agent can inhibit the binding between reagents, or in preferred embodiments the quenching agent inactivates at least one and more preferably all reagents which may contribute to an interfering optical signal.

The reagent or reagents with which the quenching agent in the waste chamber reacts to reduce the interference can be, for example without limitation, an unbound enzyme and/or an unbound substrate. The reagent with which the quenching agent reacts to reduce the interference is generally not as important as the reduction of the interference itself. The quenching agent in the waste chamber can vary depending on the type of assay that is being performed in the fluidic device. Preferably a subject quenching agent reduces an interfering optical signal by at least about 95%, at least about 98%, at least about 99%, at least about 99.9%, or more. In a preferred embodiment the quenching agent reduces an interfering optical signal by about 99%. In another preferred embodiments the waste chamber reduces optical interference by at least about 99.5%. In more preferred embodiments the quenching agent reduces optical interference by at least about 99.9%. The quenching effect should preferably be rapid, typically within a few minutes and more preferably within a few seconds. It also should preferably be as complete as possible to ensure the interference is reduced as much as possible. In preferred embodiments the inactivation of the enzyme reaction should be more than 99% complete before the optical signal indicative of the presence of the analyte in the sample is detected by any detection mechanism that may be used with the fluidic device as described herein.

In some embodiments the quenching agent can be a chemical that is a strong non-volatile acid such as trichloroacetic acid or its salt sodium trichloracetate. The substance can also be a strong alkali such as sodium hydroxide. Other strong non-volatile acids and strong alkalis can be used in accordance with the present invention. In some embodiments the quenching agent reduces the optical interference by inhibiting the enzyme. In an ELISA, for example, the quenching agent can interfere with the enzyme's ability to convert the substrate to produce a luminescent signal. Exemplary enzyme inhibitors include lactose which inhibits the action of β-galactosidase on luminogenic galactosides, and phosphate salts which inhibit phosphatases. In other embodiments the quenching agent can reduce the interference by denaturing the enzyme. Once denatured the enzyme it is unable to carry out it enzymatic function and the optical interference is suppressed or reduced. Exemplary denaturants include detergents such as sodium dodecyl sulfate (SDS), heavy metal salts such as mercuric acetate, or chelating agents such as EDTA which can sequester metal ions essential for activity of certain enzymes such as alkaline phosphatase. All types of surfactants may be used including cationic (CTMAB) and anionic (SDS). In a preferable embodiment, azobenzene compounds can be used as a quenching agent.

In addition, the quenching agent can be a non-denaturing chemical that is incompatible with enzyme activity. Exemplary chemicals include buffers and the like that change the pH to a value where the enzyme becomes inactive and thus unable to catalyze the production of the interfering signal.

Furthermore, the quenching agent can be, for example, an organic charge-transfer molecule, including 7,7,8,8-tetracyanoquinodimethane (TCNQ), 2,3,5,6-tetrafluoro-7,7,8,8-tetracyanoquinodimethane (TFTCNQ), carbon nanotubes, mordant yellow 10 (MY) and 4-amino-1,1$^1$-azobenzene-3, 4$^1$-disulfonic acid (AB). In preferred embodiments the azobenzene compounds are MY and AB, as they are considerably more water-soluble than TCNQ, TFTCNQ and carbon nanotubes. The structure of AB is shown below in:

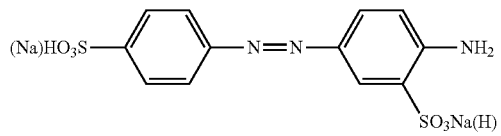

In some embodiments the quenching agent can be heavy atoms such as iodine which reduces the interference by quenching a fluorescent species used to enhance a chemiluminescent signal. In other embodiments the quenching agent can be an organic compound with an absorption spectrum overlapping the fluorescence emission spectrum of a fluorescent species used to enhance a chemiluminescent signal. In some embodiments such a quenching agent is a dark quencher such as a dispersion of carbon particles (for example, carbon black, charcoal). Carbon can inactivate chemiluminescence by absorbing actives species, and it is also a very good quenching agent that is substantially incapable of emitting fluorescence.

In yet some embodiments the quenching agent can be an antioxidant, which can reduce the interference by disrupting the chemiluminescent reaction. Quenching agents that may be used in some embodiments of the invention include but are not limited to Trolox, butylated hydroxytoluene (BHT), ascorbic acid, citric acid, retinol, carotenoid terpenoids, non-carotenoid terpenoids, phenolic acids and their esters, and bioflavinoids.

In still other embodiments, the quenching agent can be a singlet oxygen quencher, which can reduce the interference by disrupting the chemiluminescent reaction. Some singlet oxygen quenchers include but are not limited to 1,4 diazabicyclo[2,2,2]octane, thiol containing compounds such as methionine or cysteine, and carotenoids such as lycopene. In general, the substance used to impregnate or saturate the absorbent material is preferably highly concentrated, typically in large molar excess of the assay reagents.

The fluidic device may be manufactured by stamping, thermal bonding, adhesives or, in the case of certain substrates, for example, glass, or semi-rigid and non-rigid polymeric substrates, a natural adhesion between the two components. In some embodiments the fluidic device is manufactured by ultrasonic or acoustic welding.

The present system also provides a fluidic device that can run a variety of assays, regardless of the analyte being detected from a bodily fluid sample. A protocol dependent on the identity of the fluidic device may be transferred from an external device where it can be stored to a reader assembly to enable the reader assembly to carry out the specific protocol on the fluidic device. In preferred embodiments, the fluidic device has an identifier (ID) that is detected or read by an identifier detector described herein. The identifier detector communicates with a communication assembly via a controller which transmits the identifier to an external device. Where desired, the external device sends a protocol stored on the external device to the communication assembly based on the identifier. The protocol to be run on the fluidic device may comprise instructions to the controller of the reader assembly to perform the protocol on the fluidic device, including but not limited to a particular assay to be run and a detection method to be performed. Once the assay is performed on the fluidic device, a signal indicative of an analyte in the bodily fluid sample is generated and detected by a detection assembly. The detected signal may then be communicated to the communications assembly, where it can be transmitted to the external device for processing, including without limitation, calculation of the analyte concentration in the sample.

In some embodiments the identifier may be a bar code identifier with a series of black and white lines, which can be read by an identifier detector such as a bar code reader, which are well known. Other identifiers could be a series of alphanumerical values, colors, raised bumps, or any other identifier which can be located on a fluidic device and be detected or read by an identifier detector. In some embodiments the identifier may comprise a storage or memory device and can transmit information to an identification detector. In some embodiments both techniques may be used.

Once a bodily fluid sample is provided to a fluidic device, it is inserted in a reader assembly. In some embodiments the fluidic device is partially inserted manually, and then a mechanical switch in the reader assembly automatically properly positions the fluidic device inside the reader assembly. Any other mechanism known in the art for inserting a disk or cartridge into a device may be used as well. In some embodiments only manual insertion may be required.

In some embodiments the reader assembly comprises an identifier detector for detecting or reading an identifier on the fluidic device, a controller for automatically controlling the detection assembly and also mechanical components of the reader assembly, for example, pumps and/or valves for controlling or directing fluid through the fluidic device, a detection device for detecting a signal created by an assay run on the fluidic device, and a communication assembly for communicating with an external device.

An identifier detector detects an identifier on the fluidic device which is communicated to a communication assembly. In some embodiments the identifier detector can be a bar code scanner-like device, reading a bar code on a fluidic device. The identifier detector may also be an LED that emits light which can interact with an identifier which reflects light and is measured by the identifier detector to determine the identity of a fluidic device.

A reader assembly preferably houses a detection assembly for detecting a signal produced by at least one assay on the fluidic device. The detection assembly may be above the fluidic device or at a different orientation in relation to the fluidic device based on, for example, the type of assay being performed and the detection mechanism being employed.

In preferred embodiments an optical detector is used as the detection device. Non-limiting examples include a photodiode, photomultiplier tube (PMT), photon counting detector, avalanche photo diode, or charge-coupled device (CCD). In some embodiments a pin diode may be used. In some embodiments a pin diode can be coupled to an amplifier to create a detection device with a sensitivity comparable to a PMT. Some assays may generate luminescence as described herein. In some embodiments chemiluminescence is detected. In some embodiments a detection assembly could include a plurality of fiber optic cables connected as a bundle to a CCD detector or to a PMT array. The fiber optic bundle could be constructed of discrete fibers or of many small fibers fused together to form a solid bundle. Such solid bundles are commercially available and easily interfaced to CCD detectors.

In some embodiments, the detection system may comprise non-optical detectors or sensors for detecting a particular parameter of a patient. Such sensors may include temperature, conductivity, potentiometric, and amperometric, for compounds that are oxidized or reduced, for example, $O_2$, $H_2O_2$, and $I_2$, or oxidizable/reducible organic compounds.

A communication assembly is preferably housed within the reader assembly and is capable of transmitting and receiving information wirelessly from an external device. Such wireless communication may be bluetooth or RTM technology. Various communication methods can be utilized, such as a dial-up wired connection with a modem, a direct link such as a T1, ISDN, or cable line. In preferred embodiments a wireless connection is established using exemplary wireless networks such as cellular, satellite, or pager networks, GPRS, or a local data transport system such as Ethernet or token ring over a local area network. In some embodiments the information is encrypted before it is transmitted over a wireless network. In some embodiments the communication assembly may contain a wireless infrared communication component for sending and receiving information.

In some embodiments the communication assembly can have a memory or storage device, for example localized RAM, in which the information collected can be stored. A storage device may be required if information can not be transmitted at a given time due to, for example, a temporary inability to wirelessly connect to a network. The information can be associated with the fluidic device identifier in the storage device. In some embodiments the communication assembly can retry sending the stored information after a certain amount of time. In some embodiments the memory device can store the information for a period of ten days before it is erased.

In preferred embodiments an external device communicates with the communication assembly within the reader assembly. An external device can wirelessly communicate with a reader assembly, but can also communicate with a third party, including without limitation a patient, medical personnel, clinicians, laboratory personnel, or others in the health care industry.

In some embodiments the external device can be a computer system, server, or other electronic device capable of storing information or processing information. In some embodiments the external device includes one or more computer systems, servers, or other electronic devices capable of storing information or processing information. In some embodiments an external device may include a database of patient information, for example but not limited to, medical records or patient history, clinical trial records, or preclinical trial records. In preferred embodiments, an external device stores protocols to be run on a fluidic device which can be transmitted to the communication assembly of a reader assembly when it has received an identifier indicating which fluidic device has been inserted in the reader assembly. In some embodiments a protocol can be dependent on a fluidic device identifier. In some embodiments the external device stores more than one protocol for each fluidic device. In other embodiments patient information on the external device includes more than one protocol. In preferred embodiments the external server stores mathematical algorithms to process a photon count sent from a communication assembly and in some embodiments to calculate the analyte concentration in a bodily fluid sample.

In some embodiment the external device can include one or more servers as are known in the art and commercially available. Such servers can provide load balancing, task management, and backup capacity in the event of failure of one or more of the servers or other components of the external device, to improve the availability of the server. A server can also be implemented on a distributed network of storage and processor units, as known in the art, wherein the data processing according to the present invention reside on workstations such as computers, thereby eliminating the need for a server.

A server can includes a database and system processes. A database can reside within the server, or it can reside on another server system that is accessible to the server. As the information in a database may contains sensitive information, a security system can be implemented that prevents unauthorized users from gaining access to the database.

One advantage of the present invention is that information can be transmitted from the external device back to not only the reader assembly, but to other parties or other external devices, for example without limitation, a PDA or cell phone. Such communication can be accomplished via a wireless network as disclosed herein. In some embodiments a calculated analyte concentration or other patient information can be sent to, for example but not limited to, medical personal or the patient.

Methods of Use

The subject apparatus and systems provide an effective means for high throughput and real-time detection of analytes present in a bodily fluid from a subject. The detection methods may be used in a wide variety of circumstances including identification and quantification of analytes that are associated with specific biological processes, physiological conditions, disorders or stages of disorders. As such, the subject apparatus and systems have a broad spectrum of utility in, for example, drug screening, disease diagnosis, phylogenetic classification, parental and forensic identification, disease onset and recurrence, individual response to treatment versus population bases, and monitoring of therapy. The subject apparatus and systems are also particularly useful for advancing preclinical and clinical stage of development of therapeutics, improving patient compliance, monitoring ADRs associated with a prescribed drug, developing individualized medicine, outsourcing blood testing from the central laboratory to the home or on a prescription basis, and monitoring therapeutic agents following regulatory approval.

Accordingly, in one embodiment, the present invention provides a method of detecting an analyte in a bodily fluid from a subject. The method involves the steps of a) providing a subject fluidic device or system; b) allowing a portion of said sample to react with assay reagents contained within said assay assembly to yield a signal indicative of the presence of said analyte in said sample; and c) detecting said signal generated from said analyte collected in said sample of bodily fluid. In one aspect, the invention may further comprise calibrating the measurement of said signal generated from said analyte based upon a measurement by said calibration unit. In another aspect, the method may further comprise the step of quantifying the amount of said analyte present in said bodily fluid based on the measurement provided by the calibration unit. The method can be employed to detect a plurality of analytes and said fluidic device comprises immunoassay reagents for said plurality of analytes.

As used herein, the term "subject" or "patient" is used interchangeably herein, which refers to a vertebrate, preferably a mammal, more preferably a human. Mammals include, but are not limited to, murines, simians, humans, farm animals, sport animals, and pets.

In some embodiments a sample of bodily fluid can first be provided to the fluidic device by any of the methods described herein. The fluidic device can then be inserted into the reader assembly. An identification detector housed within the reader assembly can detect an identifier of the fluidic device and communicate the identifier to a communication assembly, which is preferably housed within the reader assembly. The communication assembly then transmits the identifier to an external device which transmits a protocol to run on the fluidic device based on the identifier to the communication assembly. In some embodiments the first step of the assay is a wash cycle where all the surfaces within the fluidic device are wetted using a wash buffer. The fluidic device is then calibrated using a calibration assembly by running the same reagents as will be used in the assay through the calibration reaction sites, and then a luminescence signal from the reactions sites is detected by the detection means, and the signal is used in calibrating the fluidic device. The sample containing the analyte is introduced into the fluidic channel. The sample may be diluted and further separated into plasma or other desired component by a filter. The sample can also be separated into plasma by use of magnetic means. The separated sample now flows through the reaction sites and analytes present therein will bind to reactants bound thereon. The plasma of the sample is then flushed out of the reaction wells into a waste chamber. Depending on the assay being run, appropriate reagents are directed through the reaction sites to carry out the assay. All the wash buffers and other reagents used in the various steps, including a calibration step, are collected in wash tanks. The signal produced in the reaction sites is then detected by any of the methods described herein.

In some embodiments the method of detecting an analyte in a bodily fluid from a subject includes metering a predetermined portion of the sample to be assayed in the sample collection unit and allowing the predetermined portion of the sample to react with assay reagents contained within the assay assembly to yield a signal indicative of the presence of the analyte in the sample.

In one embodiment, the subject collects a sample of bodily fluid with the sample dilution syringe. The syringe can be inverted to re-suspend any magnetizable particles contained therein. The sample can enter the syringe through a capillary tube. In an embodiment measuring an analyte in a blood sample, the subject performs a fingerstick and touches the outer end of the glass capillary to the blood so that blood is drawn by capillary action and fills the capillary with a volume. In preferable embodiments, the sample volume is known. In some embodiments, the sample volume is in the range of about 5-20 microliters.

The sample dilution syringe is reinserted into device after collecting the sample. The entire device is then inserted into the reader (instrument). In a preferred embodiment, the rest of the steps of the method for conducting an assay are performed automatically by a reader, optionally under program control through a wireless link with a server.

The instrument pushes a piston vertically so that the seal of the sample dilution syringe are displaced downwards until fluid connection is made with a hole in fluid communication with the capillary tube. The sample and diluent are displaced completely into the well and mixed together by a moving magnetic field provided by the instrument. No liquid proceeds down the capillary tube as it is sealed at its distal end by a feature in the instrument. The sample collection unit allows for a precise sample dilution to occur because, at least, the sample dilution syringe is adapted to provide a predetermined volume of diluted sample to the sample collection well because of the capillary tube and a precise volume of diluent is stored in the sample dilution syringe. Because the diluent volume is accurately filled during manufacturing, the sample is diluted with a high degree of precision.

In an embodiment analyzing a blood sample, the red blood cells in a diluted sample co-agglutinate with the magnetizable particles aided by a solution phase antibody.

In another embodiment, a method and system is provided to obtain a plasma sample substantially free of red blood cells from a blood sample from the sample collection unit. When conducting an immunoassay, the analytes are typically contained in the blood plasma, and the red blood cells can interfere with a reaction.

The sample is transferred from the sample dilution syringe to a sample collection well in the device. The instrument contains a method of offering a magnetic force to the sample collection well. In the case of blood analysis, after a short time, the magnetically susceptible mass of red cells and magnetizable particles are held in the well by the magnetic force. By removing the red blood cells, a blood sample analyzed by the invention is intended to only comprise plasma and diluent. The plasma and diluent can also be referred to herein as a diluted plasma sample.

The sample cannot proceed from the sample collection well until a seal the well and a fluidic channel is opened by the instrument. When the seal between the channel and the instrument is opened, the sample moves by capillarity through the fluid channel and vias.

In a preferable embodiment of the invention, the instrument precisely and accurately controls the temperature of the device. In a further embodiment, the temperature is in the range of about 30-40 degrees Celsius.

As the sample flows through the device, it passes through a fluidic channel with electrodes located within the channel. The conductivity of the sample can be measured at this point of the method. The method of measuring the conductivity of a sample is described later herein.

In an embodiment, the sample is a blood sample that has had the red blood cells removed from the sample. The sample has also been diluted with a diluent. The resulting diluted plasma sample passes through the assay assembly for analysis.

Before or after the conductivity of the sample has been measured, the sample passes to one or more reaction sites. At the reaction sites, the analytes bind to their respective capture surfaces. Once the analytes have bound to the reaction site, the sample is displaced after a known time by the liquid reagents in turn flowing in the reverse direction to that by which the sample entered the channel.

Each assay has its own set of reagents that flow uniquely to the appropriate capture surfaces. Flow is initiated by forcing each reservoir onto the corresponding needle until the needle completely pierces the lower septum of the vial containing the reagent. Liquid movement is propelled by plungers in the instrument that engage the top septum of each reagent reservoir. The plungers push the reagent through the needles and into the reagent manifold then into the fluidic channel. Each step for delivering the reagent to the reaction site can be timed precisely and accurately. After one reagent has been delivered and reacted, it can be displaced by another reagent. The displaced reagent can then travel into a waste chamber surrounding the reaction site and be captured by an absorbent material in the waste chamber.

In a preferable embodiment, the final step in the assay is the reaction between enzyme captured on the capture surfaces and a chemiluminogenic substrate. There is a known relationship between the analyte concentration and the rate of production of photons. This rate can be measured by the instrument.

A variety of assays may be performed on a fluidic device according to the present invention to detect an analyte of interest in a sample. A wide diversity of labels is available in the art that can be employed for conducting the subject assays. In some embodiments labels are detectable by spectroscopic, photochemical, biochemical, immunochemical, or chemical means. For example, useful nucleic acid labels include 32P, 35S, fluorescent dyes, electron-dense reagents, enzymes, biotin, dioxigenin, or haptens and proteins for which antisera or monoclonal antibodies are available. A wide variety of labels suitable for labeling biological components are known and are reported extensively in both the scientific and patent literature, and are generally applicable to the present invention for the labeling of biological components. Suitable labels include radionucleotides, enzymes, substrates, cofactors, inhibitors, fluorescent moieties, chemiluminescent moieties, bioluminescent labels, or colorimetric labels. Reagents defining assay specificity optionally include, for example, monoclonal antibodies, polyclonal antibodies, proteins, or other polymers such as affinity matrices, carbohydrates or lipids. Detection can proceed by any of a variety of known methods, including spectrophotometric or optical tracking of radioactive, fluorescent, or luminescent markers, or other methods which track a molecule based upon size, charge or affinity. A detectable moiety can be of any material having a detectable physical or chemical property. Such detectable labels have been well-developed in the field of gel electrophoresis, column chromatography, solid substrates, spectroscopic techniques, and the like, and in general, labels useful in such methods can be applied to the present invention. Thus, a label includes without limitation any composition detectable by spectroscopic, photochemical, biochemical, immunochemical, electrical, optical thermal, or other chemical means.

In some embodiments the label is coupled directly or indirectly to a molecule to be detected such as a product, substrate, or enzyme, according to methods well known in the art. As indicated above, a wide variety of labels are used, with the choice of label depending on the sensitivity required, ease of conjugation of the compound, stability requirements, available instrumentation, and disposal provisions. Non radioactive labels are often attached by indirect means. Generally, a receptor specific to the analyte is linked to a signal generating moiety. Sometimes the analyte receptor is linked to an adaptor molecule (such as biotin or avidin) and the assay reagent set includes a binding moiety (such as a biotinylated reagent or avidin) that binds to the adaptor and to the analyte. The analyte binds to a specific receptor on the reaction site. A labeled reagent can form a sandwich-like complex in which the analyte is in the center. The reagent can also compete with the analyte for receptors on the reaction site or bind to vacant receptors on the reaction site not occupied by analyte. The label is either inherently detectable or covalently bound to a signal system, such as a detectable enzyme, a fluorescent compound, a chemiluminescent compound, or a chemiluminogenic. A number of ligands and anti-ligands can be used. Where a ligand has a natural anti-ligand, for example, biotin, thyroxine, digoxigenin, and cortisol, it can be used in conjunction with labeled, anti-ligands. Alternatively, any haptenic or antigenic compound can be used in combination with an antibody.

In some embodiments the label can also be conjugated directly to signal generating compounds, for example, by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, and umbelliferone. Chemiluminescent compounds include dioxetanes, luciferin, and 2,3-dihydrophthalazinediones, such as luminol.

Methods of detecting labels are well known to those of skill in the art. Thus, for example, where the label is radioactive, means for detection include scintillation counting or photographic films as in autoradiography. Where the label is a fluorescent label, it may be detected by exciting the fluorochrome with the appropriate wavelength of light and detecting the resulting fluorescence by, for example, microscopy, visual inspection, via photographic film, by the use of electronic detectors such as digital cameras, charge coupled devices (CCDs) or photomultipliers and phototubes, or other detection device. Similarly, enzymatic labels are detected by providing appropriate substrates for the enzyme and detecting the resulting reaction product. Finally, simple colorimetric labels are often detected simply by observing the color associated with the label. For example, conjugated gold often appears pink, while various conjugated beads appear the color of the bead.

In some embodiments the detectable signal may be provided by luminescence sources. "Luminescence" is the term commonly used to refer to the emission of light from a substance for any reason other than a rise in its temperature. In general, atoms or molecules emit photons of electromagnetic energy (for example, light) when then move from an "excited state" to a lower energy state (usually the ground state). If exciting cause is a photon, the luminescence process is referred to as "photoluminescence". If the exciting cause is an electron, the luminescence process is referred to as "electroluminescence". More specifically, electroluminescence results from the direct injection and removal of electrons to form an electron-hole pair, and subsequent recombination of the electron-hole pair to emit a photon. Luminescence which results from a chemical reaction is usually referred to as "chemiluminescence". Luminescence produced by a living organism is usually referred to as "bioluminescence". If photoluminescence is the result of a spin-allowed transition (for example, a single-singlet transition, triplet-triplet transition), the photoluminescence process is usually referred to as "fluorescence". Typically, fluorescence emissions do not persist after the exciting cause is removed as a result of short-lived excited states which may rapidly relax through such spin-allowed transitions. If photoluminescence is the result of a spin-forbidden transition (for example, a triplet-singlet transition), the photoluminescence process is usually referred to as "phosphorescence". Typically, phosphorescence emissions persist long after the exciting cause is removed as a result of long-lived excited states which may relax only through such spin-forbidden transitions. A "luminescent label" may have any one of the above-described properties.

Suitable chemiluminescent sources include a compound which becomes electronically excited by a chemical reaction and may then emit light which serves as the detectable signal or donates energy to a fluorescent acceptor. A diverse number of families of compounds have been found to provide chemiluminescence under a variety or conditions. One family of compounds is 2,3-dihydro-1,4-phthalazinedione. A frequently used compound is luminol, which is a 5-amino compound. Other members of the family include the 5-amino-6,7,8-trimethoxy- and the dimethylamino[ca] benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters, for example, p-nitrophenyl and a peroxide such as hydrogen peroxide, under basic conditions. Other useful chemiluminescent compounds that are also known include —N-alkyl acridinum esters and dioxetanes. Alternatively, luciferins may be used in conjunction with luciferase or lucigenins to provide bioluminescence.

In some embodiments immunoassays are run on the fluidic device. While competitive binding assays, which are well known in the art, may be run in some embodiments, in preferred embodiments a two-step method is used which eliminates the need to mix a conjugate and a sample before exposing the mixture to an antibody, which may be desirable when very small volumes of sample and conjugate are used, as in the fluidic device of the present invention. A two-step assay has additional advantages over the competitive binding assays when use with a fluidic device as described herein. It combines the ease of use and high sensitivity of a sandwich (competitive binding) immunoassay with the ability to assay small molecules.

In an exemplary two-step assay, the sample containing analyte first flows over a reaction site containing antibodies. The antibodies bind the analyte present in the sample. After the sample passes over the surface, a solution with analyte conjugated to a marker at a high concentration is passed over the surface. The conjugate saturates any of the antibodies that have not yet bound the analyte. Before equilibrium is reached and any displacement of pre-bound unlabeled analyte occurs, the conjugate is washed off. The amount of conjugate bound to the surface is then measured by the appropriate technique, and the detected conjugate is inversely proportional to the amount of analyte present in the sample.

An exemplary measuring technique for a two-step assay is a chemiluminescence enzyme immunoassay. As is known in the field, the marker can be a commercially available marker such as dioxitane-phosphate, which is not luminescent but becomes luminescent after hydrolysis by, for example, alkaline phosphatase. An enzyme such as alkaline phosphatase is also passed over the substrate to cause the marker to luminesce. In some embodiments the substrate solution is supplemented with enhancing agents such as, without limitation, fluorescein in mixed micelles, soluble polymers, or PVC which create a much brighter signal than the luminophore alone. Moreover, an alkaline phosphatase conjugate with a higher turnover number than that used in the commercial assay is employed. This allows signal generation to proceed much more rapidly and a higher overall signal is achieved. Use of a two-step binding assay thus contributes to higher sensitivity capabilities of the present invention.

Additionally, TOSCA is less sensitive to matrix effects than other methodologies. This allows one to work with samples that have not been extensively pre-processed using standard laboratory techniques such as, for example, solid phase extraction and chromatography. Compared to competitive binding assay, for all sample preparations (and dilutions), TOSCA has better sensitivity than competitive binding assays.

The term "analytes" according to the present invention includes without limitation drugs, prodrugs, pharmaceutical agents, drug metabolites, biomarkers such as expressed proteins and cell markers, antibodies, serum proteins, cholesterol, polysaccharides, nucleic acids, biological analytes, biomarker, gene, protein, or hormone, or any combination thereof. At a molecular level, the analytes can be polypeptide glycoprotein, polysaccharide, lipid, nucleic acid, and a combination thereof.

Of particular interest are biomarkers are associated with a particular disease or with a specific disease stage. Such analytes include but are not limited to those associated with autoimmune diseases, obesity, hypertension, diabetes, neuronal and/or muscular degenerative diseases, cardiac diseases, endocrine disorders, any combinations thereof.

Of also interest are biomarkers that are present in varying abundance in one or more of the body tissues including heart, liver, prostate, lung, kidney, bone marrow, blood, skin, bladder, brain, muscles, nerves, and selected tissues that are affected by various disease, such as different types of cancer (malignant or non-metastatic), autoimmune diseases, inflammatory or degenerative diseases.

Also of interest are analytes that are indicative of a microorganism. Exemplary microorganisms include but are not limited to bacterium, virus, fungus and protozoa. Analytes that can be detected by the subject method also include blood-born pathogens selected from a non-limiting group that consists of *Staphylococcus epidermidis*, *Escherichia coli*, methicillin-resistant *Staphylococcus aureus* (MSRA), *Staphylococcus aureus*, *Staphylococcus hominis*, *Enterococcus faecalis*, *Pseudomonas aeruginosa*, *Staphylococcus capitis*, *Staphylococcus warneri*, *Klebsiella pneumoniae*, *Haemophilus influnzae*, *Staphylococcus simulans*, *Streptococcus pneumoniae* and *Candida albicans*.

Analytes that can be detected by the subject method also encompass a variety of sexually transmitted diseases selected from the following: gonorrhea (*Neisseria gorrhoeae*), syphilis (*Treponena pallidum*), clamydia (*Clamyda tracomitis*), nongonococcal urethritis (*Ureaplasm urealyticum*), yeast infection (*Candida albicans*), chancroid (*Haemophilus ducreyi*), trichomoniasis (*Trichomonas vaginalis*), genital herpes (HSV type I & II), HIV I, HIV II and hepatitis A, B, C, G, as well as hepatitis caused by TTV.

Additional analytes that can be detected by the subject methods encompass a diversity of respiratory pathogens including but not limited to *Pseudomonas aeruginosa*, methicillin-resistant *Staphlocoocccus aureus* (MSRA), *Klebsiella pneumoniae*, *Haemophilis influenzae*, *Staphlococcus aureus*, *Stenotrophomonas maltophilia*, *Haemophilis parainfluenzae*, *Escherichia coli*, *Enterococcus faecalis*, *Serratia marcescens*, *Haemophilus parahaemolyticus*, *Enterococcus cloacae*, *Candida albicans*, *Moraxiella*

*catarrhalis, Streptococcus pneumoniae, Citrobacter freundii, Enterococcus faecium, Klebsella oxytoca, Pseudomonas fluorscens, Neiseria meningitidis, Streptococcus pyogenes, Pneumocystis carinii, Klebsella pneumoniae Legionella pneumophila, Mycoplasma pneumoniae*, and *Mycobacterium tuberculosis*.

Listed below are additional exemplary markers according to the present invention: Theophylline, CRP, CKMB, PSA, Myoglobin, CA125, Progesterone, TxB2, 6-keto-PGF-1-alpha, and Theophylline, Estradiol, Lutenizing hormone, High sensitivity CRP, Triglycerides, Tryptase, Low density lipoprotein Cholesterol, High density lipoprotein Cholesterol, Cholesterol, IGFR.

Exemplary liver markers include without limitation LDH, (LD5), (ALT), Arginase 1 (liver type), Alpha-fetoprotein (AFP), Alkaline phosphatase, Alanine aminotransferase, Lactate dehydrogenase, and Bilirubin.

Exemplary kidney markers include without limitation TNFa Receptor, Cystatin C, Lipocalin-type urinary prostaglandin D, synthatase (LPGDS), Hepatocyte growth factor receptor, Polycystin 2, Polycystin 1, Fibrocystin, Uromodulin, Alanine, aminopeptidase, N-acetyl-B-D-glucosaminidase, Albumin, and Retinol-binding protein (RBP).

Exemplary heart markes include without limitation Troponin I (TnI), Troponin T (TnT), CK, CKMB, Myoglobin, Fatty acid binding protein (FABP), CRP, D-dimer, S-100 protein, BNP, NT-proBNP, PAPP-A, Myeloperoxidase (MPO), Glycogen phosphorylase isoenzyme BB (GPBB), Thrombin Activatable Fibrinolysis Inhibitor (TAFI), Fibrinogen, Ischemia modified albumin (IMA), Cardiotrophin-1, and MLC-I (Myosin Light Chain-I).

Exemplary pancrease markers include without limitation Amylase, Pancreatitis-Assocoated protein (PAP-1), and Regeneratein proteins (REG).

Exemplary muscle tissue markers include without limitation Myostatin.

Exemplary blood markers include without limitation Erythopoeitin (EPO).

Exemplary bone markers include without limitation, Cross-linked N-telopeptides of bone type I collagen (NTx) Carboxyterminal cross-linking telopeptide of bone collagen, Lysyl-pyridinoline (deoxypyridinoline), Pyridinoline, Tartrate-resistant acid phosphatase, Procollagen type I C propeptide, Procollagen type I N propeptide, Osteocalcin (bone gla-protein), Alkaline phosphatase, Cathepsin K, COMP (Cartillage Oligimeric Matrix Protein), Osteocrin Osteoprotegerin (OPG), RANKL, sRANK, TRAP 5 (TRACP 5), Osteoblast Specific Factor 1 (OSF-1, Pleiotrophin), Soluble cell adhesion molecules, sTfR, sCD4, sCD8, sCD44, and Osteoblast Specific Factor 2 (OSF-2, Periostin).

In some embodiments markers according to the present invention are disease specific. Exemplary cancer markers include without limitation PSA (total prostate specific antigen), Creatinine, Prostatic acid phosphatase, PSA complexes, Prostrate-specific gene-1, CA 12-5, Carcinoembryonic Antigen (CEA), Alpha feto protein (AFP), hCG (Human chorionic gonadotropin), Inhibin, CAA Ovarian C1824, CA 27.29, CA 15-3, CAA Breast C1924, Her-2, Pancreatic, CA 19-9, Carcinoembryonic Antigen, CAA pancreatic, Neuron-specific enolase, Angiostatin DcR3 (Soluble decoy receptor 3), Endostatin, Ep-CAM (MK-1), Free Immunoglobulin Light Chain Kappa, Free Immunoglobulin Light Chain Lambda, Herstatin, Chromogranin A, Adrenomedullin, Integrin, Epidermal growth factor receptor, Epidermal growth factor receptor-Tyrosine kinase, Pro-adrenomedullin N-terminal 20 peptide, Vascular endothelial growth factor, Vascular endothelial growth factor receptor, Stem cell factor receptor, c-kit/KDR, KDR, and Midkine.

Exemplary infectious disease markers include without limitation Viremia, Bacteremia, Sepsis, PMN Elastase, PMN elastase/α1-PI complex, Surfactant Protein D (SP-D), HBVc antigen, HBVs antigen, Anti-HBVc, Anti-HIV, T-supressor cell antigen, T-cell antigen ratio, T-helper cell antigen, Anti-HCV, Pyrogens, p24 antigen, Muramyl-dipeptide.

Exemplary diabetes markers include without limitation C-Peptide, Hemoglobin A1c, Glycated albumin, Advanced glycosylation end products (AGEs), 1,5-anhydroglucitol, Gastric Inhibitory Polypeptide, Glucose, Hemoglobin, ANGPTL3 and 4.

Exemplary inflammation markers include without limitation Rheumatoid factor (RF), Antinuclear Antibody (ANA), C-reactive protein (CRP), Clara Cell Protein (Uteroglobin).

Exemplary allergy markers include without limitation Total IgE and Specific IgE.

Exemplary autism markers include without limitation Ceruloplasmin, Metalothioneine, Zinc, Copper, B6, B12, Glutathione, Alkaline phosphatase, and Activation of apo-alkaline phosphatase.

Exemplary coagulation disorders markers include without limitation b-Thromboglobulin, Platelet factor 4, Von Willebrand factor.

In some embodiments a marker may be therapy specific. COX inhibitors include without limitation TxB2 (Cox-1), 6-keto-PGF-1-alpha (Cox 2), 11-Dehydro-TxB-1a (Cox-1).

Other markers of the present include without limitation Leptin, Leptin receptor, and Procalcitonin, Brain S100 protein, Substance P, 8-Iso-PGF-2a.

Exemplary geriatric markers include without limitation, Neuron-specific enolase, GFAP, and S100B.

Exemplary markers of nutritional status include without limitation Prealbumin, Albumin, Retinol-binding protein (RBP), Transferrin, Acylation-Stimulating Protein (ASP), Adiponectin, Agouti-Related Protein (AgRP), Angiopoietin-like Protein 4 (ANGPTL4, FIAF), C-peptide, AFABP (Adipocyte Fatty Acid Binding Protein, FABP4) Acylation-Stimulating Protein (ASP), EFABP (Epidermal Fatty Acid Binding Protein, FABP5), Glicentin, Glucagon, Glucagon-Like Peptide-1, Glucagon-Like Peptide-2, Ghrelin, Insulin, Leptin, Leptin Receptor, PYY, RELMs, Resistin, amd sTfR (soluble Transferrin Receptor).

Exemplary markers of Lipid metabolism include without limitation Apo-lipoproteins (several), Apo-A1, Apo-B, Apo-C-II, Apo-D, Apo-E.

Exemplary coagulation status markers include without limitation Factor I: Fibrinogen, Factor II: Prothrombin, Factor III: Tissue factor, Factor IV: Calcium, Factor V: Proaccelerin, Factor VI, Factor VII: Proconvertin, Factor VIII: Anti-hemolytic factor, Factor IX: Christmas factor, Factor X: Stuart-Prower factor, Factor XI: Plasma thromboplastin antecedent, Factor XII: Hageman factor, Factor XIII: Fibrin-stabilizing factor, Prekallikrein, High-molecular-weight kininogen, Protein C, Protein S, D-dimer, Tissue plasminogen activator, Plasminogen, a2-Antiplasmin, Plasminogen activator inhibitor 1 (PAI1).

Exemplary monoclonal antibodies include those for EGFR, ErbB2, and IGF1R.

Exemplary tyrosine kinase inhibitors include without limitation Abl, Kit, PDGFR, Src, ErbB2, ErbB 4, EGFR, EphB, VEGFR1-4, PDGFRb, FLt3, FGFR, PKC, Met, Tie2, RAF, and TrkA.

Exemplary Serine/Threoline Kinas Inhibitors include without limitation AKT, Aurora A/B/B, CDK, CDK (pan), CDK1-2, VEGFR2, PDGFRb, CDK4/6, MEK1-2, mTOR, and PKC-beta.

GPCR targets include without limitation Histamine Receptors, Serotonin Receptors, Angiotensin Receptors, Adrenoreceptors, Muscarinic Acetylcholine Receptors, GnRH Receptors, Dopamine Receptors, Prostaglandin Receptors, and ADP Receptors.

In a separate embodiment, the present invention provides a method of monitoring more than one pharmacological parameter useful for assessing efficacy and/or toxicity of a therapeutic agent. The method comprises subjecting a sample of bodily fluid from a subject administered with the therapeutic agent to a fluidic device for monitoring said more than one pharmacological parameter, said fluidic device comprising at least one sample collection unit, and an assay assembly comprising reaction reagents; allowing said sample of bodily fluid to react with immunoassay reagents to yield detectable signals indicative of the values of the more than one pharmacological parameter from said sample; and detecting said detectable signal generated from said sample of bodily fluid. Where desired, the method further involves repeating the steps at a time interval prompted by a wireless signal communicated to the subject.

For the purposes of this invention, a "therapeutic agent" is intended to include any substances that have therapeutic utility and/or potential. Such substances include but are not limited to biological or chemical compounds such as a simple or complex organic or inorganic molecule, peptides, proteins (for example antibodies) or a polynucleotide (for example anti-sense). A vast array of compounds can be synthesized, for example polymers, such as polypeptides and polynucleotides, and synthetic organic compounds based on various core structures, and these are also included in the term "therapeutic agent". In addition, various natural sources can provide compounds for screening, such as plant or animal extracts, and the like. It should be understood, although not always explicitly stated that the agent is used alone or in combination with another agent, having the same or different biological activity as the agents identified by the inventive screen. The agents and methods also are intended to be combined with other therapies.

Pharmacodynamic (PD) parameters according to the present invention include without limitation physical parameters such as temperature, heart rate/pulse, blood pressure, and respiratory rate, and biomarkers such as proteins, cells, and cell markers. Biomarkers could be indicative of disease or could be a result of the action of a drug. Pharmacokinetic (PK) parameters according to the present invention include without limitation drug and drug metabolite concentration. Identifying and quantifying the PK parameters in real time from a sample volume is extremely desirable for proper safety and efficacy of drugs. If the drug and metabolite concentrations are outside a desired range and/or unexpected metabolites are generated due to an unexpected reaction to the drug, immediate action may be necessary to ensure the safety of the patient. Similarly, if any of the pharmacodynamic (PD) parameters fall outside the desired range during a treatment regime, immediate action may have to be taken as well.

In preferred embodiments physical parameter data is stored in or compared to store profiles of physical parameter data in a bioinformatics system which may be on an external device incorporating pharmacogenomic and pharmacokinetic data into its models for the determination of toxicity and dosing. Not only does this generate data for clinical trials years prior to current processes but also enables the elimination of current disparities between apparent efficacy and actual toxicity of drugs through real-time continuous monitoring. During the go/no go decision process in clinical studies, large scale comparative population studies can be conducted with the data stored on the database. This compilation of data and real-time monitoring allows more patients to enter clinical trials in a safe fashion earlier than currently allowed. In another embodiment biomarkers discovered in human tissue studies can be targeted by the device for improved accuracy in determining drug pathways and efficacy in cancer studies.

In another embodiment, the present invention provides a method of detecting at least two distinct analytes of different concentrations in a bodily fluid from a subject comprises providing a fluidic device comprising a sample collection unit, an assay assembly, and a plurality of channels in fluid communication with said sample collection unit and/or said assay assembly; allowing a sample of bodily fluid to react with a plurality of reactants contained in said assay assembly to yield signals indicative of the concentrations of said at least two analytes; and detecting said signals that are indicative of the presence or absence of the at least two distinct analytes, wherein said signals are detectable over a range of 3 orders of magnitude.

Currently, a need exists for the detecting more than one analyte where the analytes are present in widely varying concentration range, for example, one analyte is in the pg/ml concentration and another is in the ng/ml concentration. TOSCA described herein has the ability to simultaneously assay analytes that are present in the same sample in a wide concentration range. Another advantage for being able to detect concentrations of different analytes present in a wide concentration range is the ability to relate the ratios of the concentration of these analytes to safety and efficacy of multiple drugs administered to a patient. For example, unexpected drug-drug interactions can be a common cause of adverse drug reactions. A real-time, concurrent measurement technique for measuring different analytes would help avoid the potentially disastrous consequence of adverse drug-drug interactions.

Being able to monitoring the rate of change of an analyte concentration or PD or PK over a period of time in a single subject, or performing trend analysis on the concentration, PD, or PK, whether they are concentrations of drugs or their metabolites, can help prevent potentially dangerous situations. For example, if glucose were the analyte of interest, the concentration of glucose in a sample at a given time as well as the rate of change of the glucose concentration over a given period of time could be highly useful in predicting and avoiding, for example, hypoglycemic events. Such trend analysis has widespread beneficial implications in drug dosing regimen. When multiple drugs and their metabolites are concerned, the ability to spot a trend and take proactive measures is often desirable.

Accordingly, the data generated with the use of the subject fluidic devices and systems can be utilized for performing a trend analysis on the concentration of an analyte in a subject.

In some embodiments, a method of detecting an analyte in a bodily fluid from a subject using an assay transmitted from an external device is provided. The method comprises providing a fluidic device comprising at least one sample collection unit and an immunoassay assembly containing immunoassay reagents; detecting said fluidic device and wirelessly transmitting an immunoassay protocol to said device; allowing a sample of bodily fluid to react with immunoassay reagents to yield a detectable signal indicative of the presence of said analyte using said transmitted immunoassay protocol; and detecting said detectable signal.

Communication between a reader assembly and an external storage device allows for a reader assembly of the present invention to download a fluidic device-specific protocol to run on the fluidic device based on the identity of the fluidic device. This allows a reader assembly to be used interchangeably with any appropriate fluidic device described herein. In addition, the external device can store a plurality of protocols associated with a given fluidic device, and depending on, for example, a subject's treatment regime or plan, different protocols can be communicated from the external device to the reader assembly to be run on the fluidic device to detect a variety of analytes. The external device can also store a plurality of protocols associated not only with a fluidic device, but also with a particular subject or subjects, such that a protocol can be associated with a subject as well as with a fluidic device.

In some embodiments, the present invention provides a business method of assisting a clinician in providing an individualized medical treatment comprises collecting at least one pharmacological parameter from an individual receiving a medication, said collecting step is effected by subjecting a sample of bodily fluid to reactants contained in a fluidic device, which is provided to said individual to yield a detectable signal indicative of said at least one pharmacological parameter; and cross referencing with the aid of a computer medical records of said individual with the at least one pharmacological parameter of said individual, thereby assisting said clinician in providing individualized medical treatment.

The present invention allows for automatic quantification of a pharmacological parameter of a patient as well as automatic comparison of the parameter with, for example, the patient's medical records which may include a history of the monitored parameter, or medical records of another group of subjects. Coupling real-time analyte monitoring with an external device which can store data as well as perform any type of data processing or algorithm, for example, provides a device that can assist with typical patient care which can include, for example, comparing current patient data with past patient data. The present invention therefore creates a business method which effectively performs at least part of the monitoring of a patient that is currently performed by medical personnel.

In some embodiments, the present invention provides a business method of monitoring a clinical trial of a pharmaceutical agent comprises collecting at least one pharmacological parameter from a subject in said clinical trial at a plurality of time intervals, said collecting step is effected at each time interval by subjecting a sample of bodily fluid from said subject to reactants contained in a fluidic device, wherein said fluidic device is provided to said subject to yield detectable signals indicative of the values of said at least one pharmacological parameter at a plurality of time intervals; comparing the detected values to a threshold value predetermined for said pharmacological parameter; notifying a clinician and/or a sponsor involved in said clinical trial when a statistically significant discrepancy exists between the detected values and the threshold value. Such business methods can provide rapidly publishing or generating early reads on new indications, both with respect to sub-patient populations and indications, as well as ameliorating safety concerns. Such methods are also amenable to conducting a trial involving multiple compounds. In this way, multiple compounds can be taken into serially in patient groups by leveraging this integrated, actionable system.

One advantage of the current invention is that assay results can be substantially immediately communicated to any third party that may benefit from obtaining the results. For example, once the analyte concentration is determined at the external device, it can be transmitted to a patient or medical personnel who may need to take further action. The communication step to a third party can be performed wirelessly as described herein, and by transmitting the data to a third party's hand held device, the third party can be notified of the assay results virtually anytime and anywhere. Thus, in a time-sensitive scenario, a patient may be contacted immediately anywhere if urgent medical action may be required.

In some embodiments a method of automatically selecting a protocol to be run on a fluidic device comprises providing a fluidic device comprising an identifier detector and an identifier; detecting said identifier with said identifier detector; transferring said identifier to an external device; and selecting a protocol to be run on said fluidic device from a plurality of protocols on said external device associated with said identifier.

By detecting each fluidic device based on an identifier associated with the fluidic device after it is inserted in the reader assembly, the system of the present invention allows for fluidic device-specific protocols to be downloaded from an external device and run on the fluidic device. In some embodiments the external device can store a plurality of protocols associated with the fluidic device or associated with a particular patient or group of patients. For example, when the identifier is transmitted to the external device, software on the external device can obtain the identifier. Once obtained, software on the external device, such as a database, can use the identifier to identify protocols stored in the database associated with the identifier. If only one protocol is associated with the identifier, for example, the database can select the protocol and software on the external device can then transmit the protocol to the communication assembly on the reader assembly. The ability to use protocols specifically associated with a fluidic device allows for any appropriate fluidic device to be used with a single reader assembly, and thus virtually any analyte of interest can be detected with a single reader assembly.

In some embodiments multiple protocols may be associated with a single identifier. For example, if it is beneficial to detect from the same patient an analyte once a week, and another analyte twice a week, protocols on the external device associated with the identifier can also each be associated with a different day of the week, so that when the identifier is detected, the software on the external device can select a specific protocol that is associated with the day of the week.

In some embodiments a patient may be provided with a plurality of fluidic devices to use to detect a variety of analytes. A subject may, for example, use different fluidic devices on different days of the week. In some embodiments the software on the external device associating the identifier with a protocol may include a process to compare the current day with the day the fluidic device is to be used based on a clinical trial for example. If for example, the two days of the week are not identical, the external device can wirelessly send notification to the subject using any of the methods described herein or known in the art to notify them that an incorrect fluidic device is in the reader assembly and also of the correct fluidic device to use that day. This example is only illustrative and can easily be extended to, for example, notifying a subject that a fluidic device is not being used at the correct time of day.

In some embodiments, the present invention provides a method of obtaining pharmacological data useful for assessing efficacy and/or toxicity of a pharmaceutical agent from a test animal utilizing the subject fluidic devices or systems.

When using laboratory animals in preclinical testing of a pharmaceutical agent, it is often necessary to kill the test subject to extract enough blood to perform an assay to detect an analyte of interest. This has both financial and ethical implications, and as such it may be advantageous to be able to draw an amount of blood from a test animal such that the animal does not need to be killed. In addition, this can also allow the same test animal to be tested with multiple pharmaceutical agents at different times, thus allowing for a more effective preclinical trial. On average, the total blood volume in a mouse, for example, is 6-8 ml of blood per 100 gram of body weight. A benefit of the current invention is that only a very small volume of blood is required to perform preclinical trials on mice or other small laboratory animals. In some embodiment between about 1 microliter and about 50 microliters are drawn. In an embodiment between about 1 microliter and 10 microliters are drawn. In preferred embodiments about 5 microliters of blood are drawn.

A further advantage of keeping the test animal alive is evident in a preclinical time course study. When multiple mice, for example, are used to monitor the levels of an analyte in a test subject's bodily fluid over time, the added variable of using multiple subjects is introduced into the trial. When, however, a single test animal can be used as its own control over a course of time, a more accurate and beneficial preclinical trial can be performed.

In some embodiments a method of automatically monitoring patient compliance with a medical treatment using the subject fluidic devices or systems is provided. The method comprises the steps of allowing a sample of bodily fluid to react with assay reagents in a fluidic device to yield a detectable signal indicative of the presence of an analyte in said sample; detecting said signal with said fluidic device; comparing said signal with a known profile associated with said medical treatment to determine if said patient is compliant or noncompliant with said medical treatment; and notifying a patient of said compliance or noncompliance.

Noncompliance with a medical treatment, including a clinical trial, can seriously undermine the efficacy of the treatment or trial. As such, in some embodiments the system of the present invention can be used to monitor patient compliance and notify the patient or other medical personnel of such noncompliance. For example, a patient taking a pharmaceutical agent as part of medical treatment plan can take a bodily fluid sample which is assayed as described herein, but a metabolite concentration, for example, detected by the reader assembly may be at an elevated level compared to a known profile that will indicate multiple doses of the pharmaceutical agent have been taken. The patient or medical personnel may be notified of such noncompliance via any or the wireless methods discussed herein, including without limitation notification via a handheld device such a PDA or cell phone. Such a known profile may be located or stored on an external device described herein.

In some embodiments noncompliance may include taking an improper dose of a pharmaceutical agent including without limitation multiple doses and no doses, or may include inappropriately mixing pharmaceutical agents. In preferred embodiments a patient is notified substantially immediately after the signal is compared with a known profile.

A patient or subject of a clinical trial may forget to take a bodily fluid sample as described herein. In some embodiments a method of alerting a patient to test a sample of bodily fluid using a fluidic device as described herein comprises providing a protocol to be run on said fluid device, said protocol located on an external device, associated with said patient, and comprising a time and date to test said sample of bodily fluid; and notifying patient to test said bodily fluid on said date and time if said sample has not been tested. In some embodiments a patient can be notified wirelessly as described herein.

A patient may be provided with a fluidic device or devices when procuring a prescription of drugs by any common methods, for example, at a pharmacy. Likewise, a clinical trial subject may be provided with such devices when starting a clinical trial. The patient or subject's contact information, including without limitation cell phone, email address, text messaging address, or other means of wireless communication, may at that time be entered into the external device and associated with the patient or subject as described herein, for example, in a database. Software on the external device may include a script or other program that can detect when a signal generated from a detection device has not yet been sent to the external device, for example at a given time, and the external device can then send an alert notifying the patient to take a bodily fluid sample.

Methods of Measuring a Plasma Dilution Ratio

In another aspect, the present invention provides a method of measuring plasma concentration in a blood sample. The method comprises the steps of running a current through the sample and measuring the conductivity of the sample. In a related but separate embodiment, the present invention provides a method of calculating an apparent dilution ratio utilized in diluting a blood sample for running a blood test. This method comprises the steps of (a) providing a plasma sample derived from a diluted blood sample; (b) measuring conductivity of the plasma sample; and d) comparing the measured conductivity to a set of predetermined values showing relationship of conductivity values and dilution ratios that are employed to dilute a blood sample, thereby calculating the apparent dilution ratio.

The device of the invention can be constructed to detect an analyte utilizing a small volume of bodily fluid. A workable volume of bodily fluid may range from about 1 microliter to about 500 microliters, from about 1 microliter to about 100 microliters, from about 1 microliter to about 50 microliters, from about 1 microliter to about 30, 20, or even 10 microliters.

When such a sample is diluted, the measurement of the analyte in the sample depends on the concentration of the sample in the sample diluent solution. Traditionally, the sample and the diluent have been carefully metered and the calculation of the concentration of the sample in a diluted solution was calculated based on the ratio of sample to diluent. In the case of dilution, there can be a target of staying within 2% of the metered volumes. This requires a precision of 0.2 microliters for a 10 microliter blood sample. In an embodiment where the sample is blood, wherein the whole blood is a somewhat viscous fluid comprising a high volume fraction (28-58%) of blood cells, it is often more difficult to meter than water or other simple aqueous liquids. It can be difficult to extract and recover blood plasma from such a small sample. The theoretical maximum recoverable volume of blood plasma from a 10 microliter blood sample with a 50% hematocrit is typically 5 microliters.

It can be advantageous to first dilute the blood sample and then remove the red cells to retrieve only a plasma diluent solution (or a plasma dilution sample). The problem introduced by this approach is that the hematocrit (the percentage of red blood cells in blood) has a wide variance, typically from ~28-58% in adults. Therefore, the volume and percentage of the blood plasma recovered can vary significantly from patient to patient. To determine the amount of analyte in a blood sample, the result needs to be concentration per the amount of plasma (or serum) to correspond with clinical laboratory results.

Furthermore, single use devices intended for point-of-care applications suffer from the risk that the user will not provide a sample of sufficient volume and the resulting analytical result will be in error. Even when the device is designed automatically to meter the correct volume of blood, users can compromise the operation of the device if the drop of blood obtained is insufficient or the user fails to contact the device to the blood drop long enough.

A method to measure the percentage of plasma in a diluted plasma sample is disclosed. The method solves some of blood processing problems described herein. Since the measurement is made after all blood cells have been removed, it can be made independent of the hematocrit. The method enables a method of pre-treating a blood sample wherein the blood is first diluted and then processed for red cell removal. Very precise metering of the initial blood sample and the diluent is no longer a strict requirement as small errors in dilution will be detected by the plasma percentage measurement. The method enables the reduction of the blood volume required by the device.

The device of the invention comprises a calibration unit, wherein the calibration unit can comprise two electrodes precisely and accurately positioned therein with fixed and precise dimensions. When diluted plasma travels over the electrodes, the plasma dilution conductivity can be measured. It is preferred that the temperature of the calibration unit is controlled and fixed. When an AC voltage is applied to the sample, the impedance is inversely related to the relative concentration of plasma.

Figure 10:
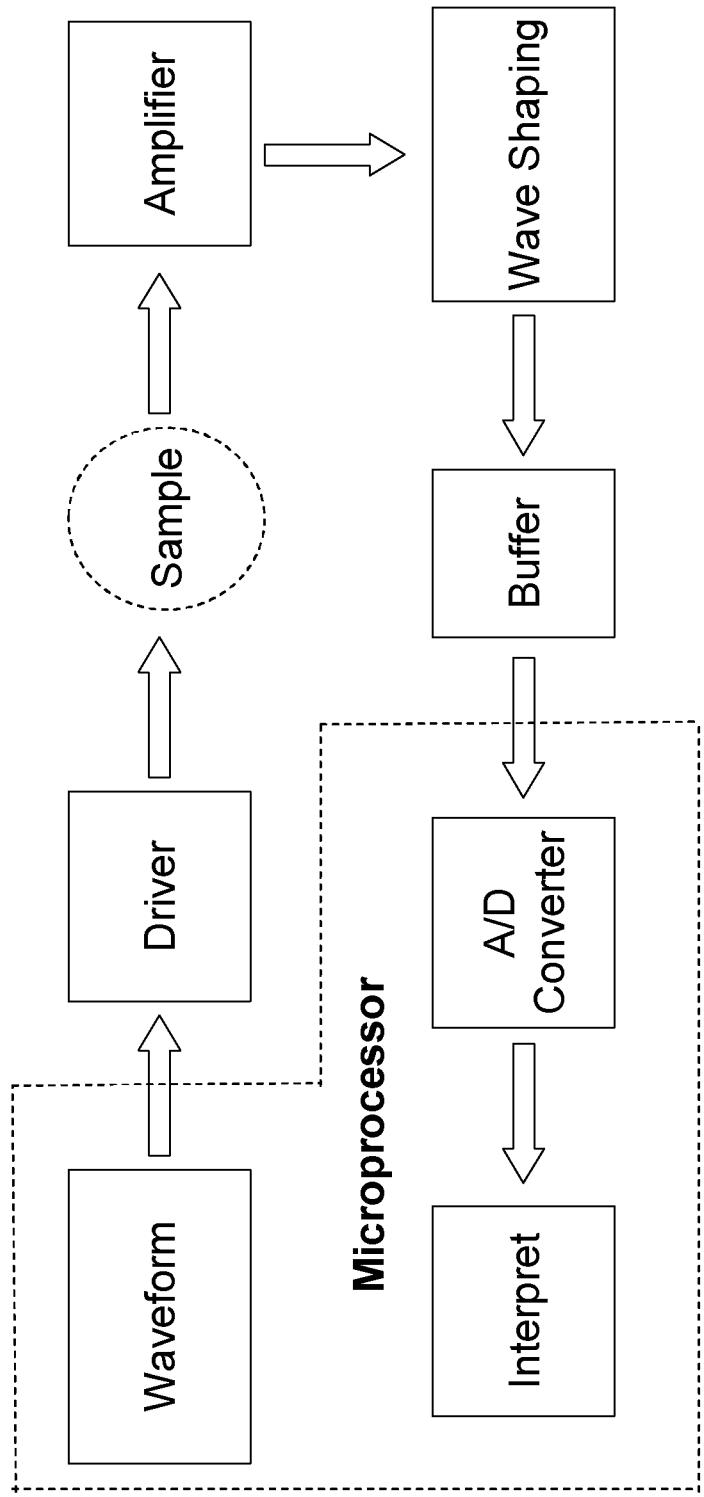
FIG. 10 demonstrates a circuit block diagram for measuring electrical conductivity of a fluidic sample.

A block diagram of the circuit is shown in FIG. 10. An AC waveform is sent by the microprocessor and driven through the sample via the electrodes. The signal is attenuated by an amount proportional to the conductivity of the sample. The resultant signal is then amplified, reshaped, buffered and sent back to the microprocessor, which then outputs a DC voltage that correlates with the conductivity of the sample.

Figure 11:
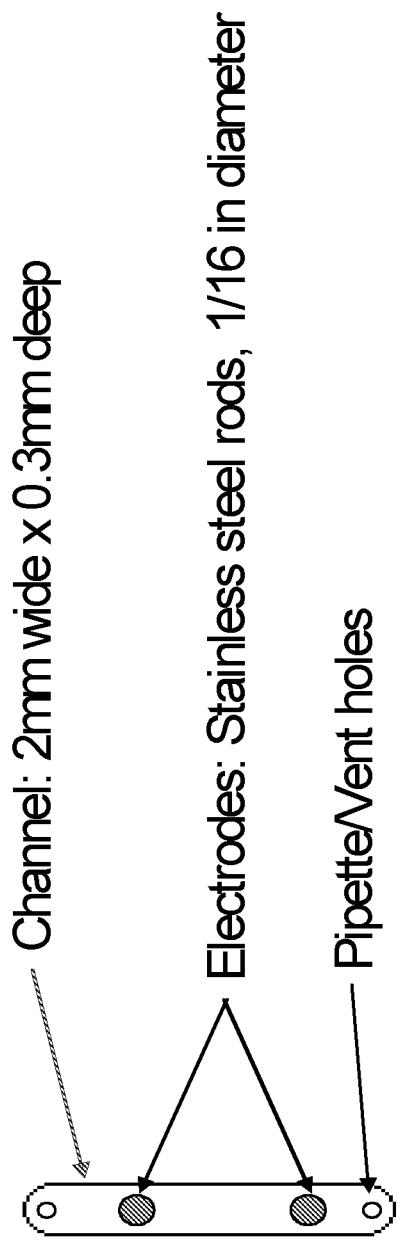
FIG. 11 demonstrates a microfluidic channel adjacent to electrodes that can be incorporated in a sample processing cartridge for measuring electronic conductivity of a fluidic sample.

In an embodiment of the device of the invention, the electrodes can be embedded in the straight sample inlet channel before a reaction site. An example of a channel adjacent to electrodes is illustrated in FIG. 11. Variations to the conductivity cell can be made to accommodate sample size and accessibility.

In an embodiment, the material of the electrodes is stainless steel. Other materials that can be used include, but are not limited to, platinum, nickel, and gold. In preferable embodiments, the material of the electrodes is inert. In some embodiments, the device of the invention is intended for single use and the electrode material is chosen based on cost efficiency.

In an example, the spacing of the electrodes is 8 mm and each electrode is 1.5 mm in diameter. In other embodiments, the spacing can be of a range of about 5-20 mm.

To measure the conductivity of a diluted plasma sample, the fact that the conductivity of whole plasma is a tightly controlled parameter can be taken advantage of. The total conductivity of blood plasma is primarily attributed to the concentration of sodium and chloride ions, which is relatively constant among most people. The sodium ion concentration in plasma varies from 136-143 mg/ml (Tietz Textbook of Clinical Chemistry, $2^{nd}$ ed. p 2206). In cases where a patient's sodium concentration falls outside this range, it is generally indicative of very serious organ damage such as kidney failure or heart failure.

Figure 12:
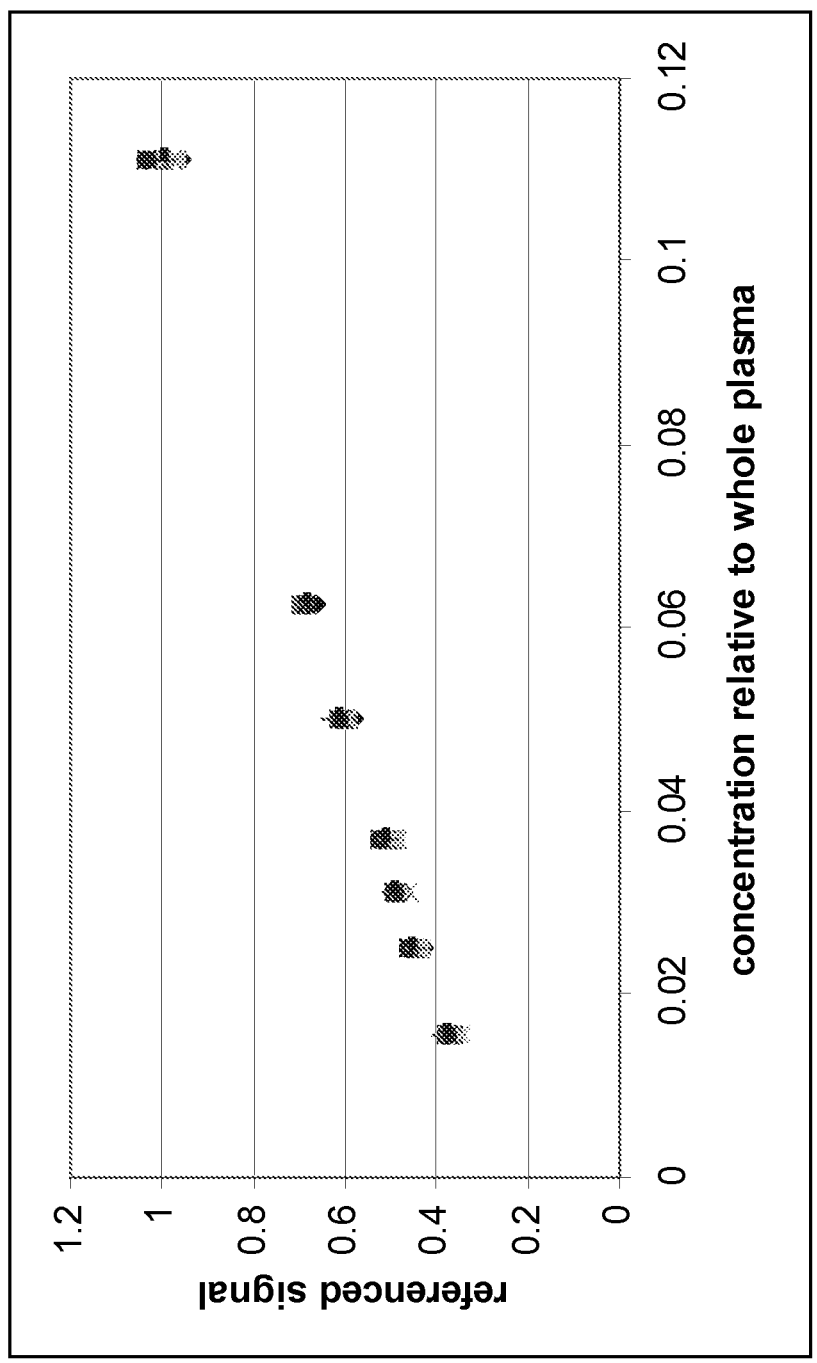
FIG. 12 demonstrates an exemplary chart comparing the concentration of plasma in a plasma dilution to the reference measurement of the plasma dilution fluidic sample.

Data from eight samples is shown in FIG. 12. Plasma was collected by spinning down whole blood in a centrifuge. The plasma was then diluted and the conductivity was measured using a prototype circuit and conductivity cell. The signal for each is referenced to a NaCl control to account for day to day changes in temperature and the conductivity cell.

The plot in FIG. 12 demonstrates a linear relationship between conductivity and relative concentration of plasma in the diluent. A diluent of low conductivity can be used so that in the diluted plasma, the dominant ionic (current carrying) species derives from the plasma. A calibration curve is created by measuring the conductivity of known dilutions of plasma. Then, the dilution of plasma can be calculated using the calibration curve.

When measuring the conductivity of sample to obtain the relationship of the conductivity and plasma concentration of a diluted sample, a set of predetermined values showing relationship of conductivity values and plasma concentrations are plotted and used as a comparison tool.

An apparent dilution ratio refers to the ratio of plasma volume to sample volume as measured by a calibration unit that is configured to measure the conductivity of a diluted sample. The apparent dilution ratio reflects the actual dilution factor resulting from adding a diluent to a test sample of bodily fluid. Errors in diluent volume, blood sample volume, and variation in the sample hematocrits results in a discrepancy between the expected dilution ratio and the actual or apparent dilution ratio. To ascertain the concentration of an analyte initially present in an undiluted fluidic sample, an accurate reading of the apparent dilution ratio is desirable.

Figure 13:
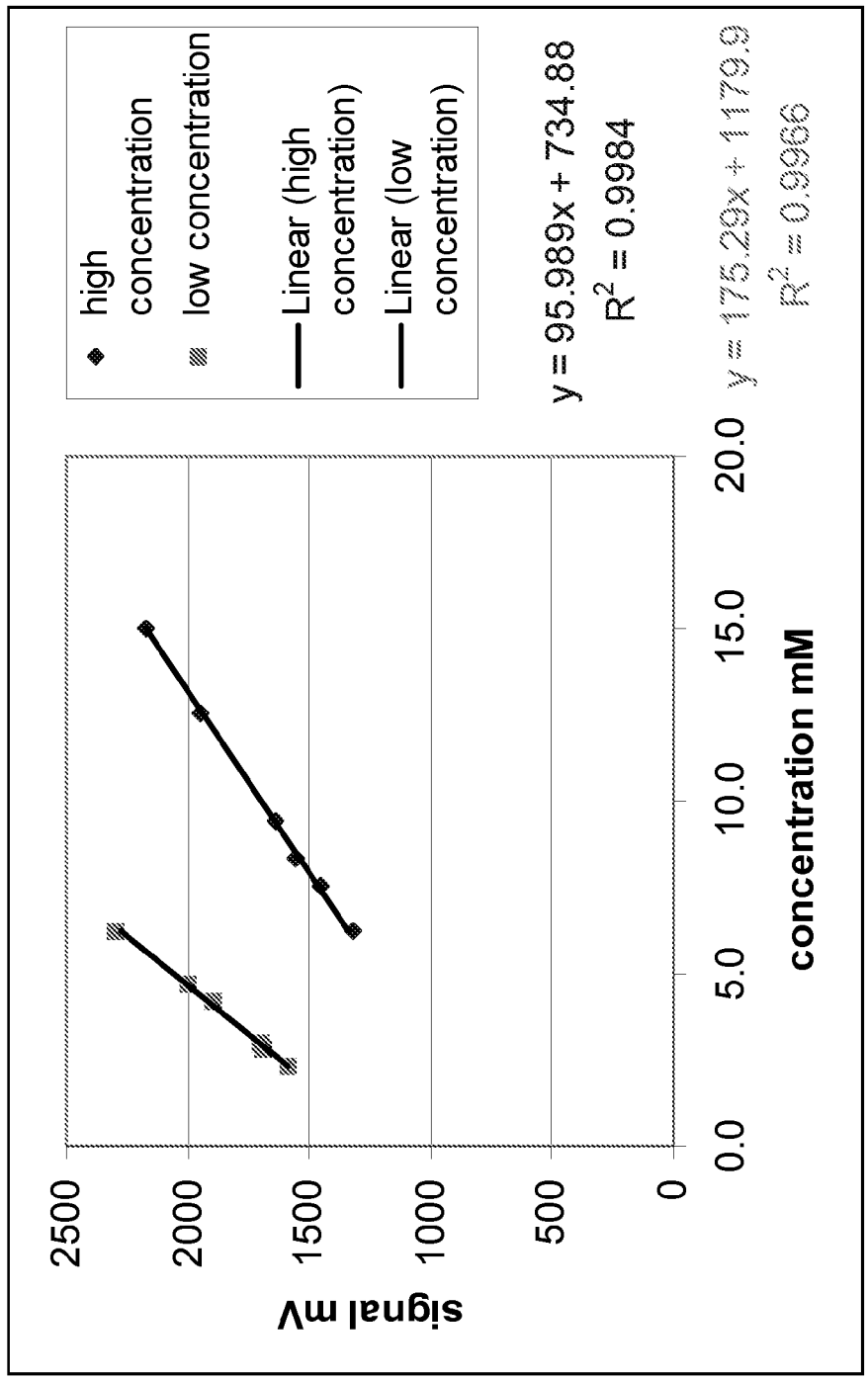
FIG. 13 demonstrates the measurable range of concentration to conductivity signal and the effect of changing the gain setting on the circuit.

In an example, the measurable range of the conductivity device was derived from the following design goals. In certain cases, blood is diluted 1:10. The conductivity measurement may need to be able to correct for errors of up ~20%. Therefore, the lowest blood dilution in range is 1:8. In other cases, blood is diluted 1:20. Again, a ~20% error must be corrected. The highest blood dilution is then 1:24. Finally, the detectable range of hematocrit is 28-58%, which makes up most of the rest of the blood sample other than the plasma. Using the following relationship between plasma dilution and blood dilution:

$$\text{Plasma dilution}=\text{Blood dilution}*(1/(1-\text{HCT \%}/100))$$

it can be determined that the measurable range of plasma dilutions needs to be 1:12-1:58. This range can account for the extremes of the design goals. As this is a fairly large range, two separate gain settings are used on the circuit depending on which dilution is required (1:10 or 1:20). This allows maximum resolution in each range of operation. The effect of changing the gain setting on the signal and the measurable range is shown in FIG. 13. The dotted red line indicates the saturation signal of the detector.

Figure 14:
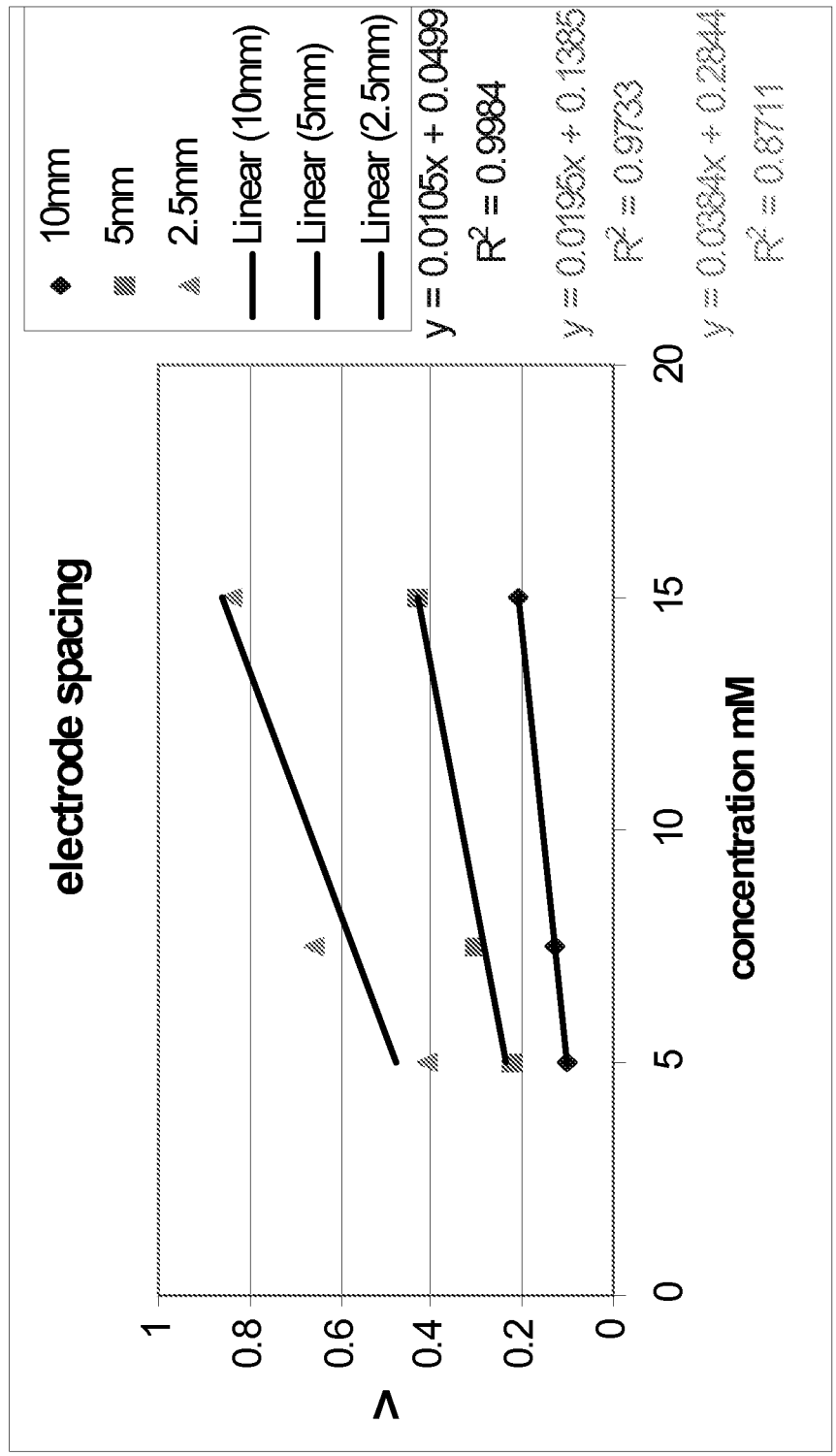
FIG. 14 demonstrates effect of the distance between electrodes adjacent to a microfluidic channel on the measurement of plasma concentration.

There are several variables that must be optimized when designing the conductivity cell. FIG. 14 demonstrates sample data showing the dependence on electrode spacing and surface area. The output shown is DC voltage, which, as explained in the description of the block diagram, is representative of the signal attenuation due to the ion carriers in the sample and is thus directly proportional to conductivity. The Figure shows that the closer the electrodes are to one another, the greater the modulation due to changes in salt concentration. However, a secondary effect is also observed. When the probes are too close together, they can begin to act as a single capacitor. Thus, as shown by the data, the background signal goes up and the response becomes increasingly noisy. In a preferable embodiment, a probe spacing of 8 mm was selected.

Figure 15:
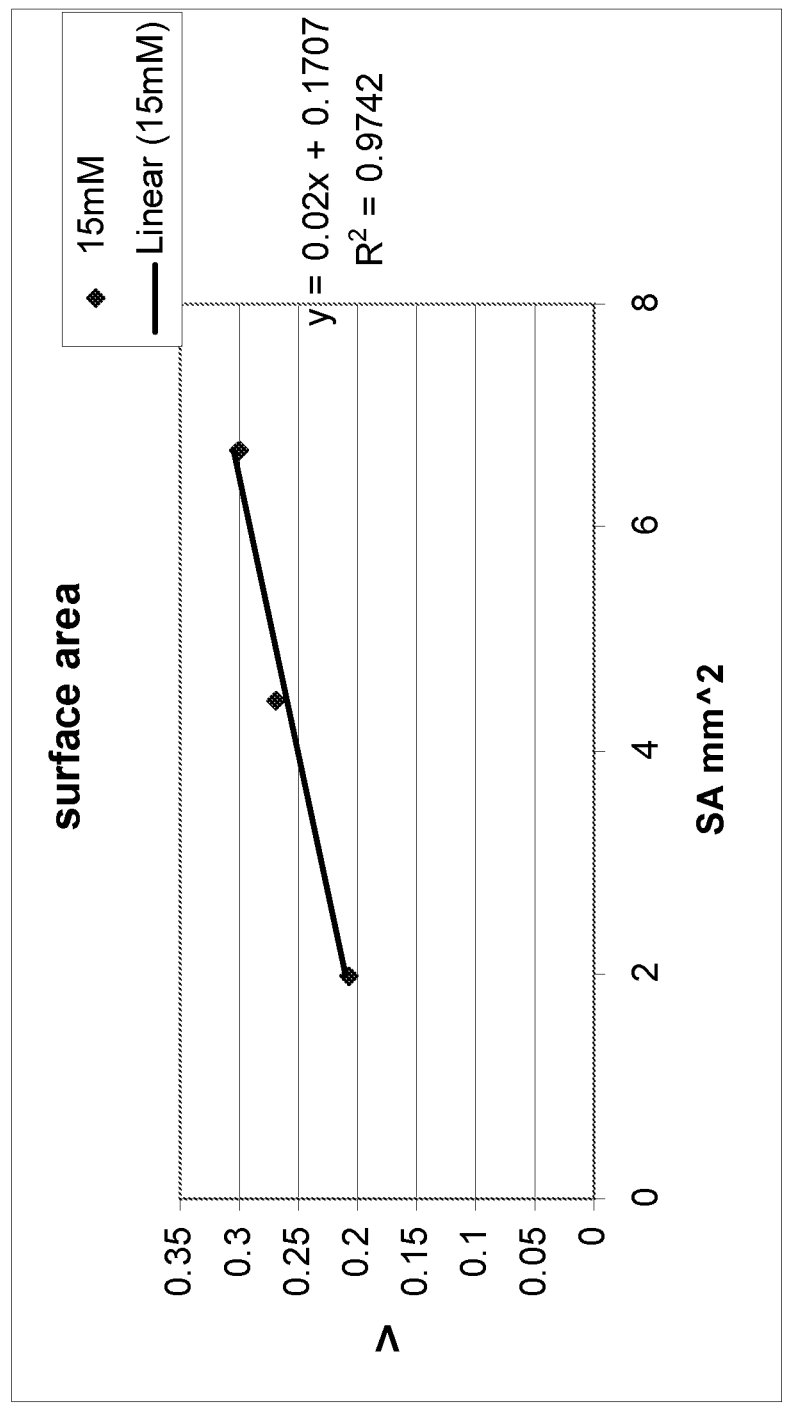
FIG. 15 illustrates of a plot of the surface area of an electrode as it relates to the voltage measured by the circuit.

Probes of different diameters were used to expose a different surface area to the same volume of fluid. The conductivity of a 40 microliter sample of 15 mM NaCl can be measured. As demonstrated in FIG. 15, a direct relationship is seen between surface area and measured signal, but the slope is fairly shallow, indicating that the signal is only moderately sensitive to surface area of the probe.

Figure 16:
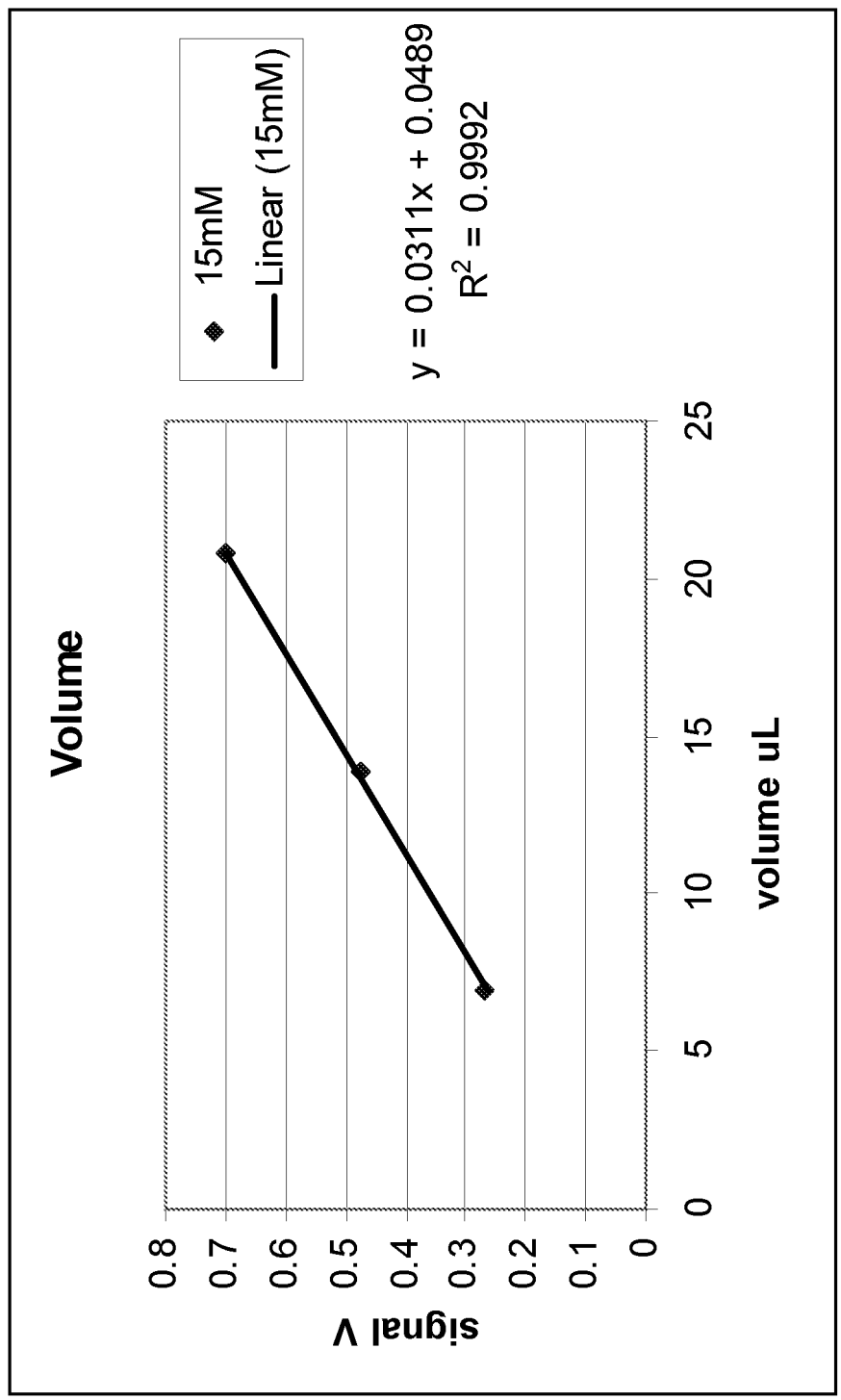
FIG. 16 demonstrates the effect of a change in volume of the plasma dilution sample on the signal measured to determine the conductivity of the sample.

A more pronounced effect of the relationship of measured signal and volume is demonstrated in FIG. 16. Smaller volumes result in fewer overall charge carriers and thus a smaller signal.

The measurement of conductivity is temperature sensitive. As the temperature of the solution increases the viscosity decreases and the ions move through the solution more rapidly. This can cause an increase in conductivity of approximately 2% per degree Celsius. This effect is shown in FIG. 16.

Figure 17:
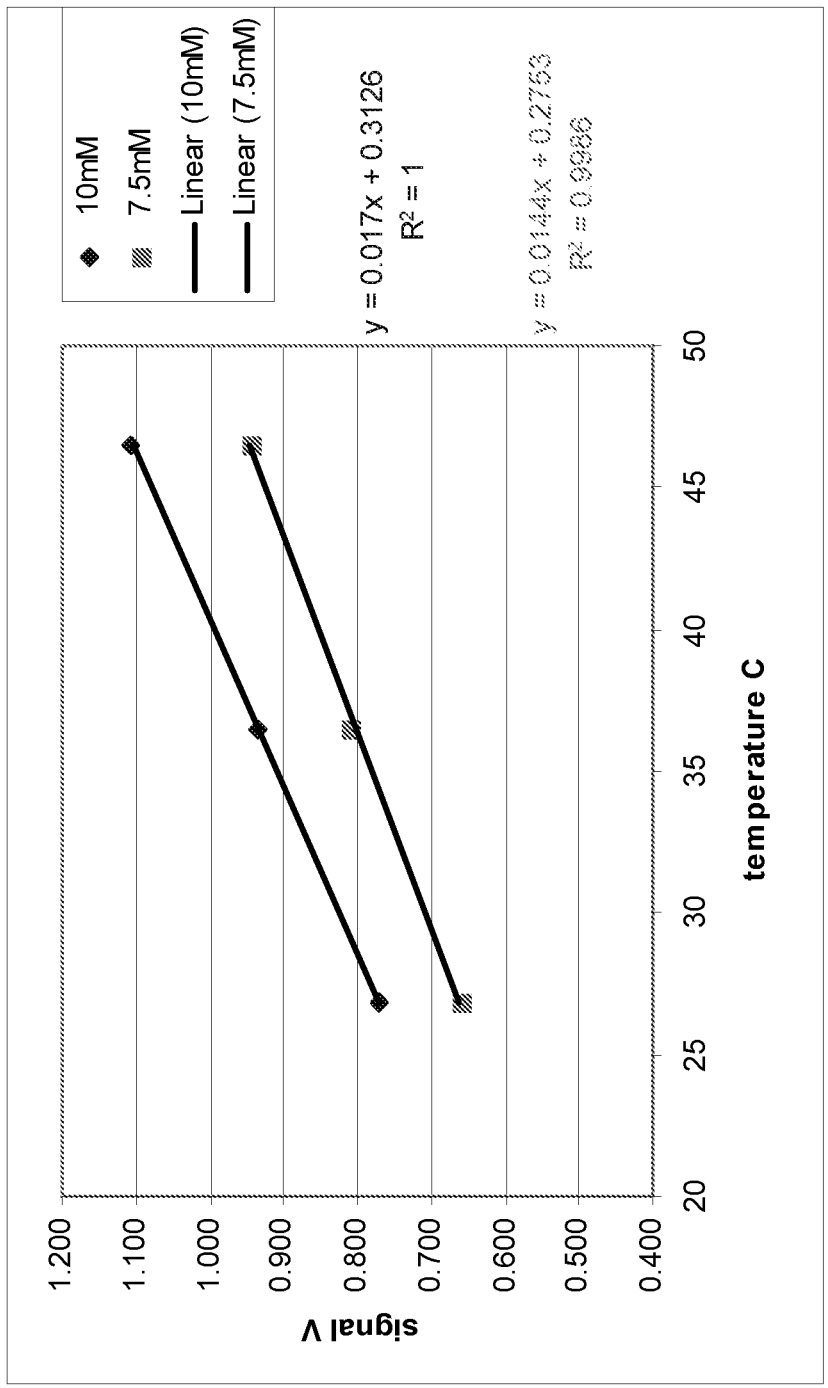
FIG. 17 demonstrates that the temperature of fluidic sample can effect the conductivity measurement.

One can account for variations in the manufacturing of the conductivity cell or variations in temperature of the conductivity cell by measuring the conductivity of a reference buffer and normalizing the signal. In FIG. 17, conductivity measurements were taken of a series of NaCl solutions (100 microliter volume). The conductivity of a reference buffer (TBS) was also taken with each probe. As seen in the first graph the larger diameter probe yields a higher conductivity for a given NaCl solution. The second graph shows all of the points normalized by the reference buffer conductivity.

Figure 18:
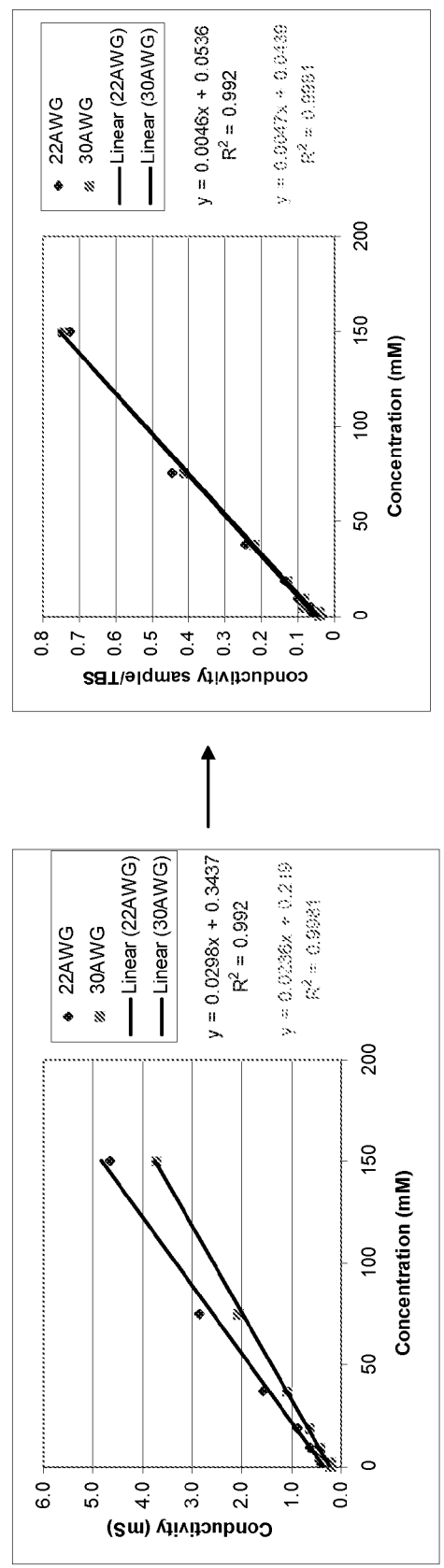
FIG. 18 illustrates a method of normalizing the conductivity measurement of the plasma concentration by measuring the conductivity of a reference buffer.

The temperature effect can also be corrected by normalizing the signal to a reference solution. The reference solution must be read at the same temperature as the corresponding samples. In the experiment demonstrated by FIG. 18, a 15 mM NaCl solution was used as a reference. The Figure shows a full set of NaCl dilutions referenced to the 15 mM solution at three different temperatures.

The ability to normalize the signal is a feature of the device. As shown in the above characterization studies, the signal is sensitive to almost all dimensional parameters of the cell as well as to temperature. The ability to normalize these variations out with a reference buffer greatly improves the reliability of the device.

Figure 19:
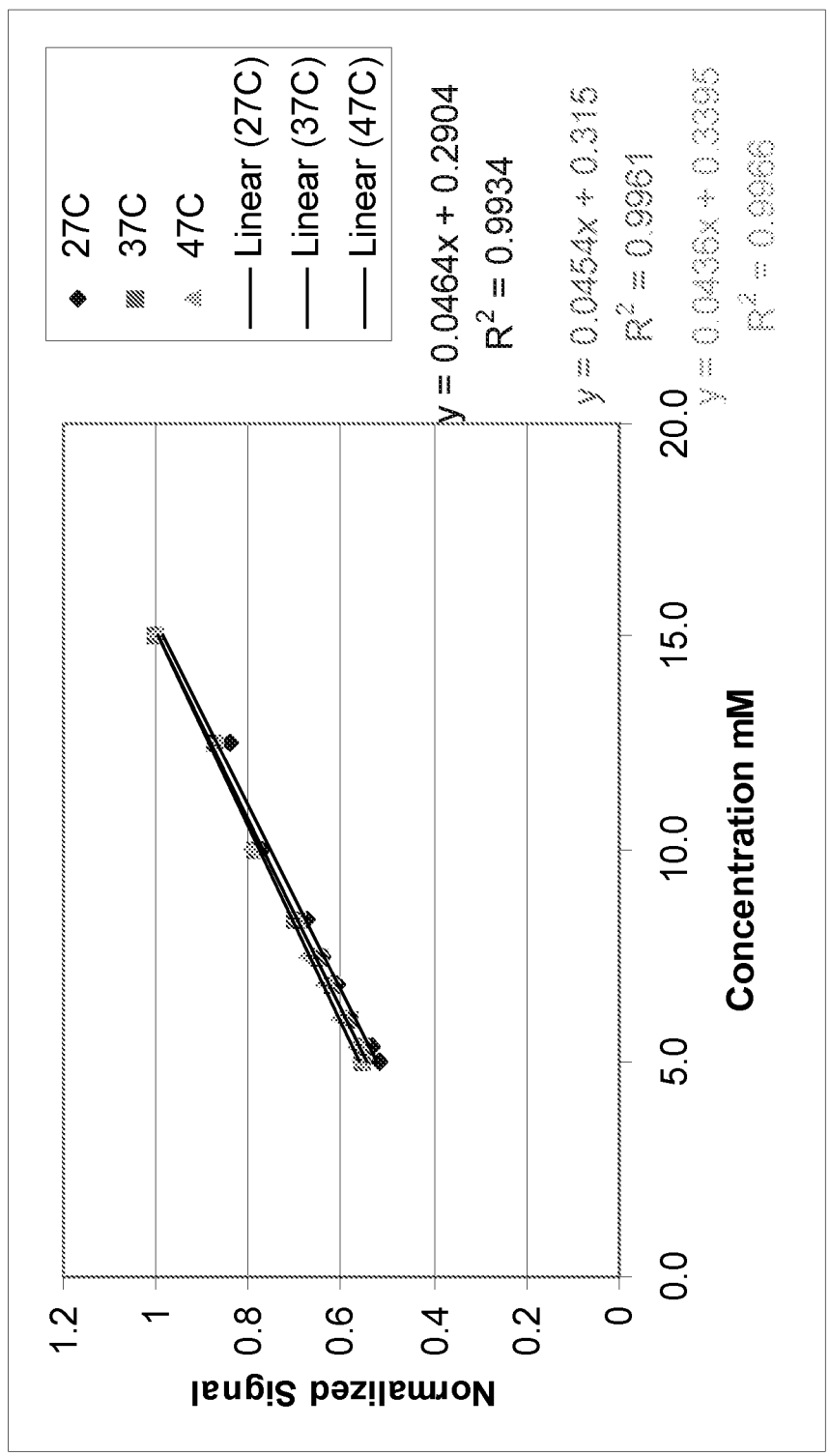
FIG. 19 demonstrates the result of a method of normalizing the conductivity measurement of the plasma concentration according to temperature of the fluidic sample.

In another embodiment, the device can measure the conductivity of a sample after the red blood cells have been removed. FIG. 19 demonstrates the effect of red blood cells on the measured conductivity of the solution. In a device that has a standard dilution of 1:10, the 10× data represents no red blood cell removal. The effect on the response is slight but there is a noticeable offset from the response of the pure salt samples. When 90% of the cells are removed (100× blood) the line basically overlays the "No blood" line. The conductivity measurement system is thus robust enough to tolerate a 10% failure in red blood cell removal.

Figure 20:
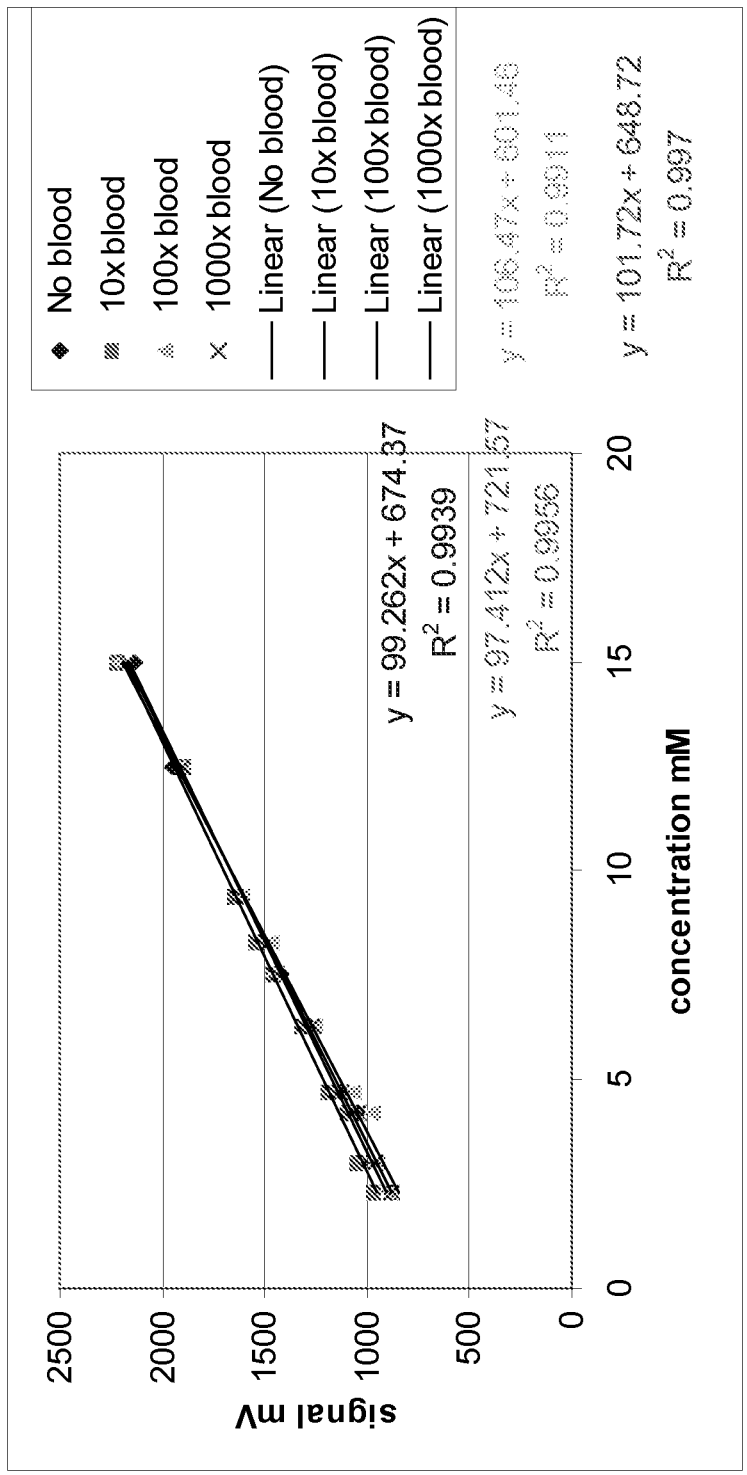
FIG. 20 demonstrates the effect of the amount of red blood cells in the plasma dilution sample on the measured conductivity of the solution.

Another possible failure mode of the blood separation mechanism is cell lysis. When the cells are lysed, their contents are released into the medium and the salt concentration of the resulting solution can become significantly altered. This is illustrated by FIG. 20.

Figure 21:
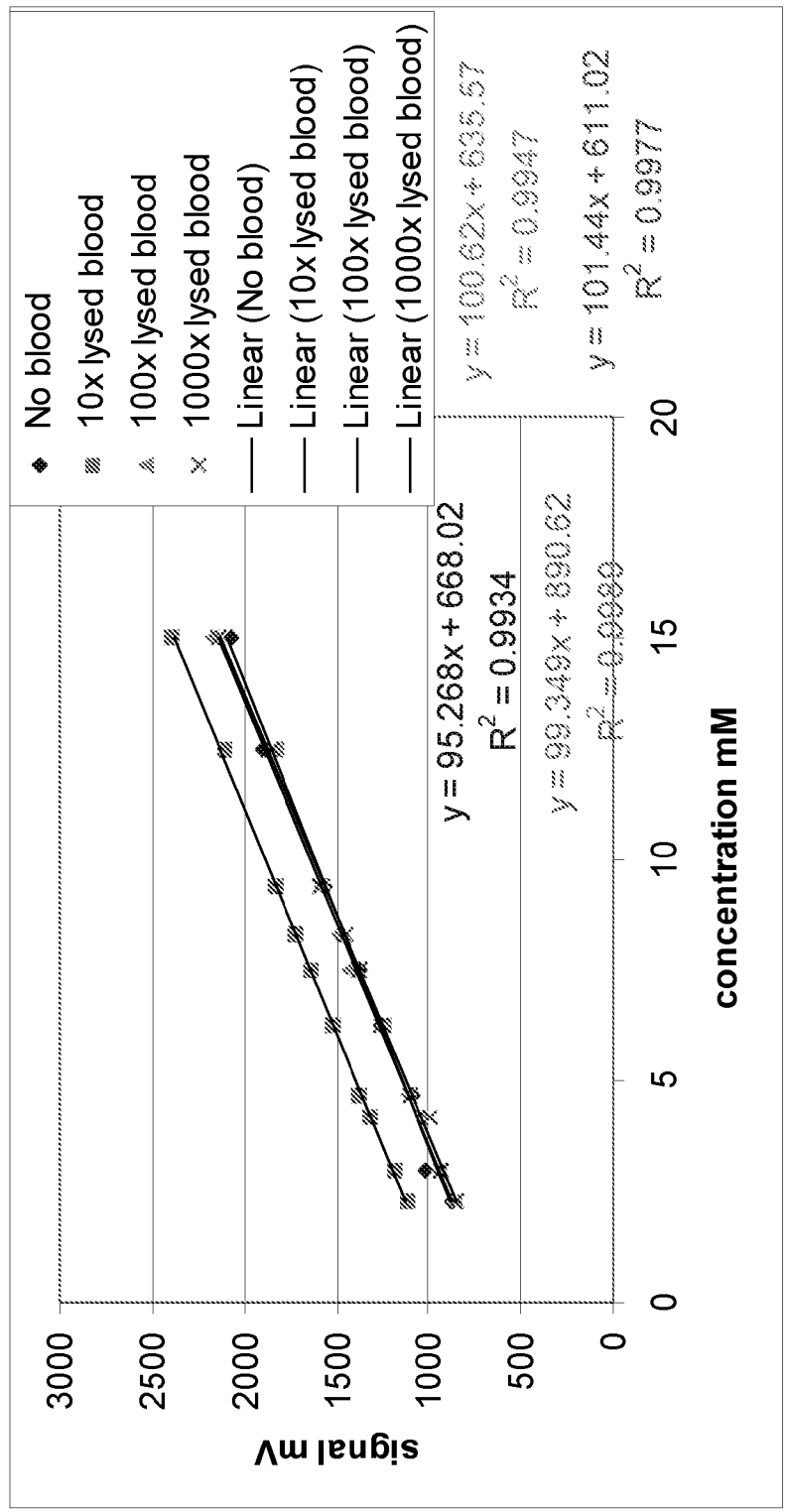
FIG. 21 demonstrates the effect of the amount of lysed red blood cells in the plasma dilution sample on the measured conductivity of the solution.

A far more pronounced offset in the case of 100% lysed blood (10× lysed blood accounting for the standard 10× dilution) is seen than in the previous case of unfiltered blood as shown in FIG. 21. However, once 90% of the lysed blood cells are removed (100× lysed blood), the curve overlays the base case of "No blood." The conductivity system is therefore also tolerant of up to 10% of the blood cells being lysed with no measurable effect on the signal.

Figure 22:
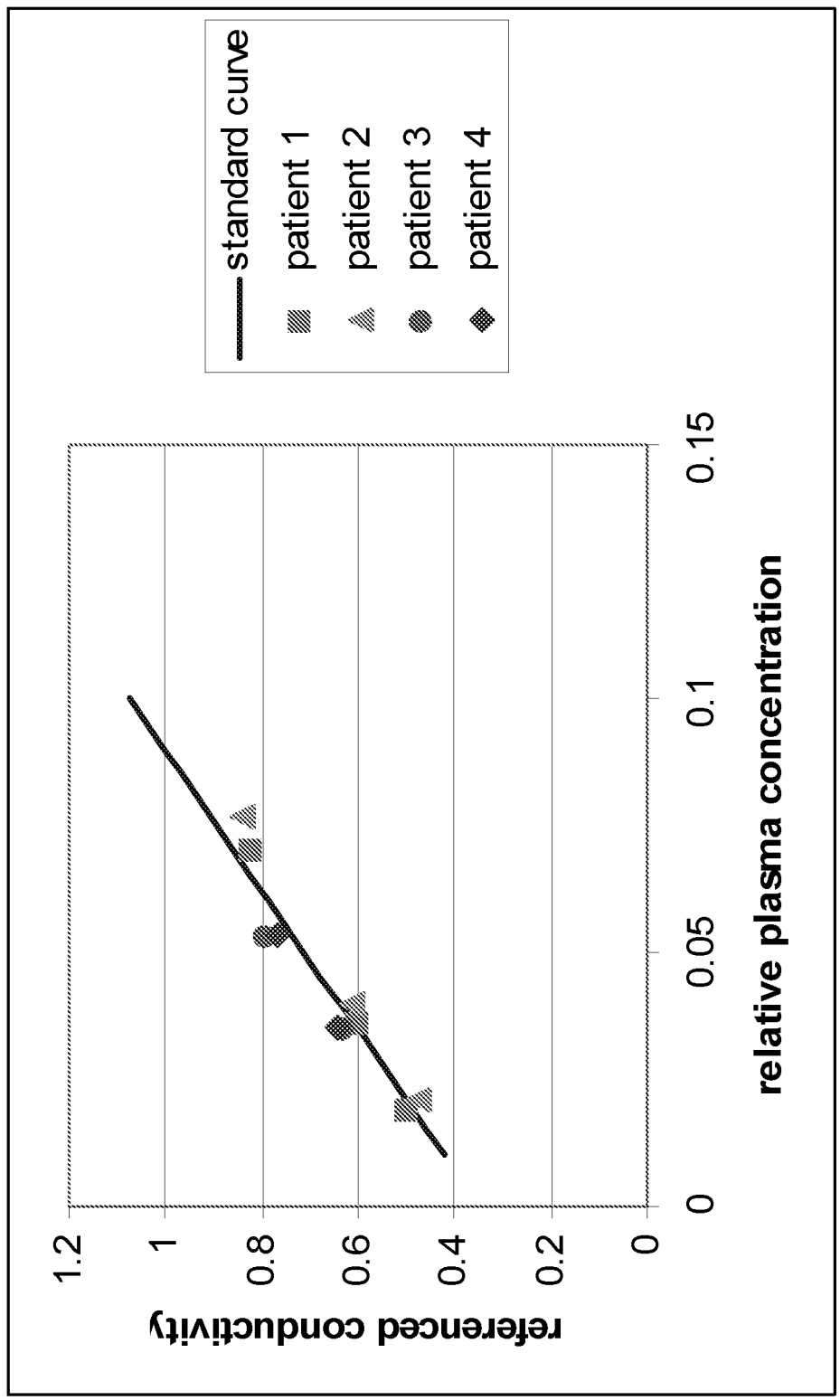
FIG. 22 illustrates the result of the measuring the plasma dilution ratio of four subjects and demonstrates a comparison to a standard calibration line.

FIG. 22 illustrates an example of clinical data showing the blood samples from four patients at varying dilutions and their relation to a standard calibration curve.

EXAMPLE

Figure 23:
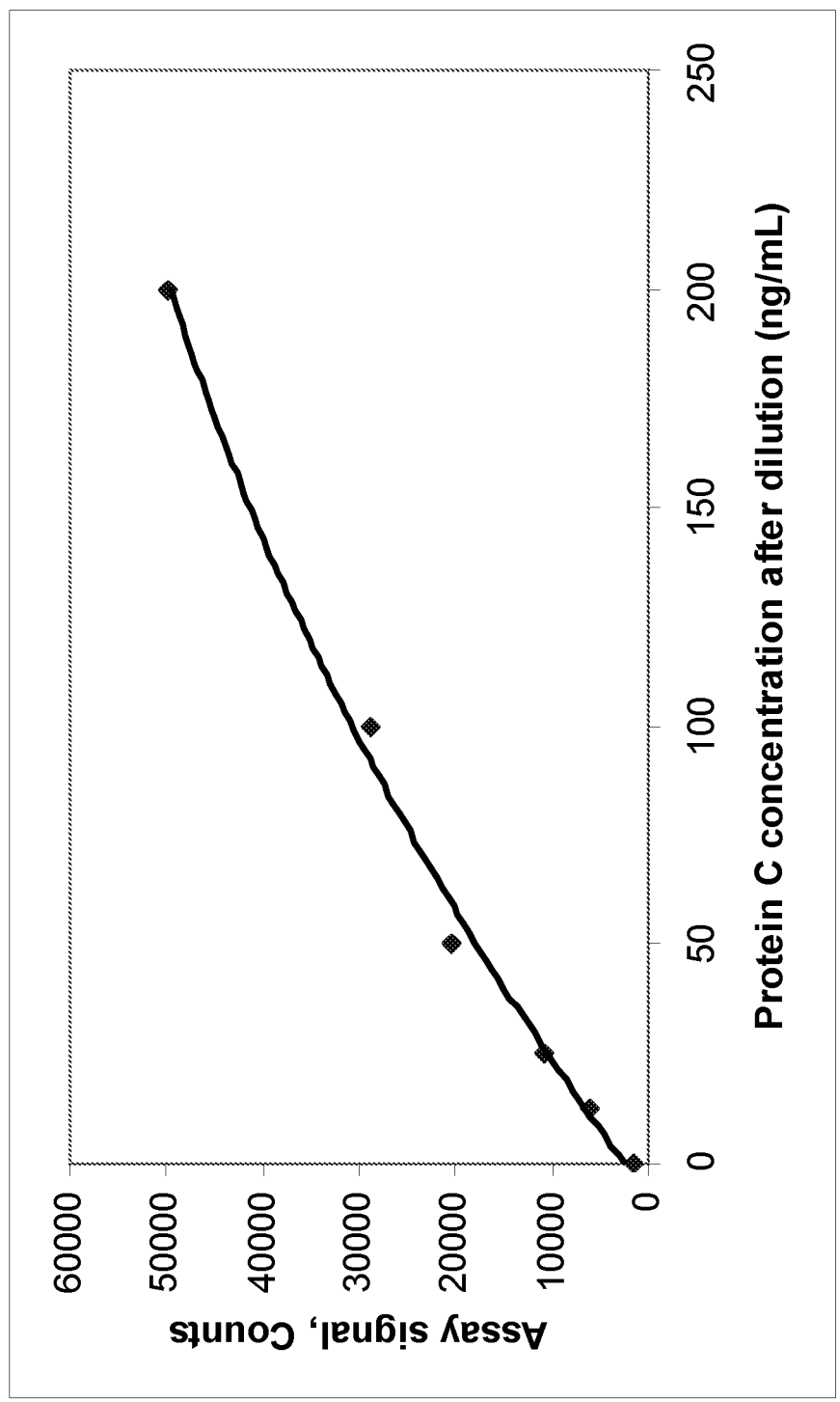
FIG. 23 illustrates an exemplary assay response for detecting Protein C in a blood sample using a fluidic processing device of the invention.

Cloned human protein-C was diluted into Tris buffer and processed in an embodiment of the device of the present invention. Monoclonal antibody against protein C was adsorbed at 10 ug/mL onto a polystyrene bottom part of a cartridge and then dried. Cartridges were then assembled with a different monoclonal antibody to protein-C labeled with alkaline phosphatase at 25 ng/mL, Tris buffered saline containing BSA (wash solution), and KPL Phosphoglo luminogenic substrate. The reaction site of the device was incubated with diluted sample and the reagents including a different monoclonal antibody to protein-C labeled with alkaline phosphatase for 10 minutes at room temperature. Following incubation, the reaction site was washed with 300 microliters of the wash solution, Tris buffered saline containing BSA. Then, the reaction site was incubated with KPL Phosphoglo luminogenic substrate for 10 minutes at room temperature. The assay signal was recorded for 0.5 ms by a photomultiplier in the instrument after the final incubation step. The results of the experiment are illustrated in FIG. 23.

What is claimed is:

1. A device comprising:
    at least a first reagent reservoir and a second reagent reservoir, wherein the first reagent reservoir comprises a first upper moveable seal, a first lower septum, and a first liquid reagent and the first liquid reagent is situated in the first reagent reservoir between the first upper moveable seal and first lower septum, and wherein the second reagent reservoir comprises a second upper moveable seal, a second lower septum, and a second liquid reagent, and the second liquid reagent is situated in the second reagent reservoir between the second upper moveable seal and the second lower septum;
    a manifold comprising a first needle and a second needle; and
    a cartridge comprising an assay assembly, wherein the assay assembly comprises a reaction site, wherein
        the first reagent reservoir is positioned adjacent to the first needle of the manifold such that the first lower septum may be completely pierced by the first needle upon forced contact between the first reagent reservoir and the first needle, and wherein upon complete piercing of the first lower septum, the first liquid reagent may enter the first needle of the manifold;
        the second reagent reservoir is positioned adjacent to the second needle of the manifold such that the second lower septum may be completely pierced by the second needle upon forced contact between the second reagent reservoir and the second needle, and wherein upon complete piercing of the second lower septum, the second liquid reagent may enter the second needle of the manifold; and
        the manifold routes the first liquid reagent and second liquid reagent from the first reagent reservoir and the second reagent reservoir, respectively, to the cartridge, via at least the first needle and the second needle.

2. The device of claim 1, further comprising a sample collection unit.

3. The device of claim 2, wherein the sample collection unit is removable from the device.

4. The device of claim 2, wherein the sample collection unit comprises a sample dilution syringe, the sample dilution syringe comprising a housing.

5. The device of claim 2, wherein the sample collection unit is fluidically connected to the reaction site of the assay assembly.

6. The device of claim 2, wherein the sample collection unit further comprises a filter.

7. The device of claim 4, wherein the sample dilution syringe contains a capillary tube, and wherein the capillary tube can be press-fit into the housing of the sample dilution syringe.

8. The device of claim 4, wherein the sample dilution syringe further contains a moveable mixing element.

9. The device of claim 8, wherein the moveable mixing element is a mixing ball.

10. The device of claim 1, wherein the device further comprises a body, and wherein the body covers the first reagent reservoir, second reagent reservoir, manifold, and cartridge.

11. The device of claim 1, wherein the first lower septum of the first reagent reservoir is in contact with the first needle of the manifold without the first needle penetrating into the portion of the first reagent reservoir containing the first liquid reagent.

12. The device of claim 1, wherein the first lower septum of the first reagent reservoir is held in place by a crimpable metal cap.

13. The device of claim 1, wherein the first reagent reservoir and second reagent reservoir each contain 100-500 microliters of liquid reagent.

14. The device of claim 1, wherein the first reagent reservoir comprises collapsible plastic.

15. The device of claim 1, wherein the reaction site of the assay assembly comprises antibodies.

16. The device of claim 1, wherein the device further comprises a waste chamber in fluidic communication with the assay assembly.

17. The device of claim 1, wherein the cartridge is made of a substantially opaque material.

18. The device of claim 1, wherein at least a portion of the cartridge is made of a clear material.

19. The device of claim 2, wherein the sample collection unit comprises a diluent.

20. The device of claim 2, wherein the sample collection unit comprises a blood sample.

* * * * *